(12) United States Patent
Wailes et al.

(10) Patent No.: US 11,672,251 B2
(45) Date of Patent: *Jun. 13, 2023

(54) HERBICIDALLY ACTIVE PYRIDYL-/PYRIMIDYL-PYRIMIDINE DERIVATIVES

(71) Applicant: Syngenta Participations AG, Basel (CH)

(72) Inventors: Jeffrey Steven Wailes, Bracknell (GB); Emma Briggs, Bracknell (GB); Neil Brian Carter, Bracknell (GB); Melloney Morris, Bracknell (GB); Joseph Andrew Tate, Bracknell (GB)

(73) Assignee: Syngenta Participations AG, Basel (CH)

( * ) Notice: Subject to any disclaimer, the term of this patent is extended or adjusted under 35 U.S.C. 154(b) by 275 days.

This patent is subject to a terminal disclaimer.

(21) Appl. No.: 16/649,628

(22) PCT Filed: Sep. 18, 2018

(86) PCT No.: PCT/EP2018/075226
§ 371 (c)(1),
(2) Date: Mar. 21, 2020

(87) PCT Pub. No.: WO2019/057720
PCT Pub. Date: Mar. 28, 2019

(65) Prior Publication Data
US 2020/0267981 A1 Aug. 27, 2020

(30) Foreign Application Priority Data
Sep. 22, 2017 (GB) ..................................... 1715318

(51) Int. Cl.
*A01N 43/54* (2006.01)
*A01N 43/78* (2006.01)
*A01N 47/40* (2006.01)
*C07D 239/42* (2006.01)
*C07D 401/04* (2006.01)
*C07D 417/14* (2006.01)

(52) U.S. Cl.
CPC ............. *A01N 43/54* (2013.01); *A01N 43/78* (2013.01); *A01N 47/40* (2013.01); *C07D 239/42* (2013.01); *C07D 401/04* (2013.01); *C07D 417/14* (2013.01)

(58) Field of Classification Search
CPC ........ A01N 43/54; A01N 43/78; A01N 47/40; C07D 239/42; C07D 401/04; C07D 417/14
See application file for complete search history.

(56) References Cited

U.S. PATENT DOCUMENTS

2003/0060629 A1 3/2003 Kuo et al.
2011/0136666 A1 6/2011 Whitingham et al.

FOREIGN PATENT DOCUMENTS

| EP | 0902026 A1 | 3/1999 |
| JP | 2001316376 A | 11/2001 |
| WO | 2009138712 A2 | 11/2009 |
| WO | 2017162521 A1 | 9/2017 |

OTHER PUBLICATIONS

Harcken, C. et al., Identification of Highly Efficacious Glucocorticoid Receptor Agonist with a Potential for Reduced Clinical Bone Side Effects, 2014, Journal of Medicinal Chemistry, vol. 57, pp. 1583-1598. (Year: 2014).*
JP2014-208631A, Machine Translation, pp. 1-284. (Year: 2014).*
JP2015-147757A, Machine Translation, pp. 1-436. (Year: 2015).*
Christian Harcken et al., Identification of Highly Efficacious Glucocorticoid Receptor Agonists with a Potential for Reduced Clinical Bone Side Effects, Journal of Medicinal Chemistry, vol. 57, No. 4, Feb. 7, 2014, pp. 1583-1598.
Database Registry [Online] Chemical Abstracts Service, Columbus, Ohio, US, Nov. 3, 2016, XP002785841, Database accession No. 2023936-95-8.
Database Registry [Online] Chemical Abstracts Service, Columbus, Ohio, US, Aug. 10, 2017, XP002785842, Compound CAS RN 2111746-60-0-C10H7F3N4, 5-Pyrimidinamine, 2-(3-pyridinyl)-4-(trifluoromethyl)-.
Compound CAS RN 1923091-82-0-C10H6BrF3N4, 5-Pyrimidinamine, 2-(5-bromo-3-pyridinyl)-4-(trifluoromethyl)-, Jun. 2, 2016.
International Searchf Report and Written Opinion for International Application PCT/EP2018/075226, dated Nov. 20, 2018.
Annex to Communication (International Preliminary Report on Patentability) dated Mar. 24, 2020.

* cited by examiner

*Primary Examiner* — Alton N Pryor
(74) *Attorney, Agent, or Firm* — BakerHostetler; Toni-Junell Herbert

(57) ABSTRACT

The present invention relates to herbicidal) active pyridyl-/pyrimidyl-pyridine derivatives, as well as to processes and intermediates used for the preparation of such derivatives. The invention further extends to herbicidal compositions comprising such derivatives, as well as to the use of such compounds and compositions in controlling undesirable plant growth: in particular the use in controlling weeds, in crops of useful plants.

7 Claims, No Drawings

HERBICIDALLY ACTIVE PYRIDYL-/PYRIMIDYL-PYRIMIDINE DERIVATIVES

CROSS-REFERENCE TO RELATED APPLICATIONS

This application is a 371 National Stage application of International Application No. PCT/EP2018/075226 filed Sep. 18, 2018 which claims priority to GB 1715318.0, filed Sep. 22, 2017, filed in the United Kingdom, the entire contents of which applications are hereby incorporated by reference.

The present invention relates to herbicidally active pyridyl-/pyrimidyl-pyrimidine derivatives, as well as to processes and intermediates used for the preparation of such derivatives. The invention further extends to herbicidal compositions comprising such derivatives, as well as to the use of such compounds and compositions in controlling undesirable plant growth: in particular the use in controlling weeds, in crops of useful plants.

Harcken et al., (2014 J. Med. Chem 57:1583-1598) describe the use of 4-chloro-2-pyridin-3-yl-pyrimidin-5-ylamine as an intermediate in the production of glucocorticoid receptor agonists.

Certain pyrido-pyridine and pyrimidino-pyridine derivatives are known from JP2014-208631, where they are stated to have activity as insecticidal agents, and in particular miticidal agents.

The present invention is based on the finding that pyridino-pyrimidine, and pyrimidino-pyrimidine, derivatives of Formula (I) as defined herein, exhibit surprisingly good herbicidal activity. Thus, in a first aspect of the invention there is provided the use of a compound of formula (I)

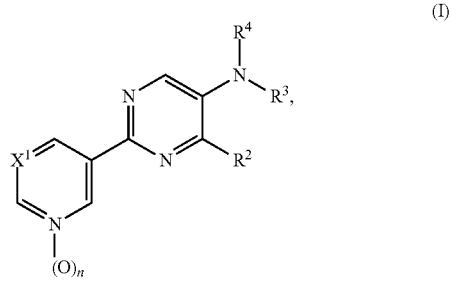

or a salt thereof, wherein:

$X^1$ is N or $CR^1$;

$R^1$ is selected from the group consisting of hydrogen, halogen, cyano, $C_1$-$C_6$alkyl, $C_3$-$C_6$cycloalkyl, $C_2$-$C_6$alkenyl, $C_2$-$C_6$alkynyl, $C_1$-$C_6$alkoxy, —C(O)OC$_1$-C$_6$alkyl, —S(O)$_p$C$_1$-C$_6$alkyl, NR$^6$R$^7$, C$_1$-C$_6$haloalkoxy and C$_1$-C$_6$haloalkyl;

$R^2$ is selected from the group consisting of halogen, cyano, nitro, $C_1$-$C_6$alkyl, $C_1$-$C_6$haloalkyl, $C_2$-$C_6$alkenyl, $C_2$-$C_6$alkynyl, $C_3$-$C_6$cycloalkyl, —C(O)OC$_1$-C$_6$alkyl, —S(O)$_p$(C$_1$-C$_6$alkyl), $C_1$-$C_6$alkoxy, $C_1$-$C_6$haloalkoxy and phenyl;

$R^3$ is selected from the group consisting of hydrogen, $C_1$-$C_6$alkyl, $C_2$-$C_6$alkenyl, $C_2$-$C_6$alkynyl, $C_2$-$C_6$haloalkenyl, $C_1$-$C_6$alkoxyC$_1$-C$_3$alkyl-, $C_1$-$C_6$haloalkyl- and —(CR$^a$R$^b$)$_q$R$^5$;

$R^a$ is hydrogen or $C_1$-$C_2$ alkyl;

$R^b$ is hydrogen or $C_1$-$C_2$ alkyl;

$R^4$ is hydrogen, $C_1$-$C_6$alkyl, $C_2$-$C_6$alkenyl, $C_2$-$C_6$alkynyl, $C_2$-$C_6$haloalkenyl, $C_1$-$C_6$alkoxyC$_1$-$C_3$alkyl-, $C_1$-$C_6$haloalkyl- and —(CR$^a$R$^b$)$_q$R$^5$; $R^5$ is —C(O)OC$_1$-C$_6$alkyl, —C$_3$-C$_{10}$cycloalkyl, -aryl, or -heteroaryl wherein said aryl and heteroaryl are optionally substituted by 1 to 3 independent $R^8$;

or $R^3$ and $R^4$ together with the nitrogen to which they are attached, form a saturated or partially unsaturated 4-6 membered ring system optionally containing 1 or 2 further heteroatoms independently selected from S in the form S(O)$_p$, O and N, wherein said ring is optionally substituted by 1 to 3 $R^8$;

$R^6$ and $R^7$ are independently selected from the group consisting of hydrogen, $C_1$-$C_6$alkyl and —C(O)OC$_1$-C$_6$alkyl;

each $R^8$ is independently selected from the group consisting of halogen, $C_1$-$C_6$ alkyl and $C_1$-$C_6$alkoxy-, $C_1$-$C_6$ haloalkyl, $C_1$-$C_6$ haloalkoxy-, cyano and S(O)$_p$(C$_1$-C$_6$alkyl);

n is 0 or 1;

p is 0, 1, or 2; and q is 0, 1, or 2, and when q is 0, $R^5$ is not —C(O)OC$_1$-C$_6$alkyl;

as a herbicide.

Certain compounds of formula (I) are novel. Thus, in a second aspect the invention provides a compound of Formula (I)

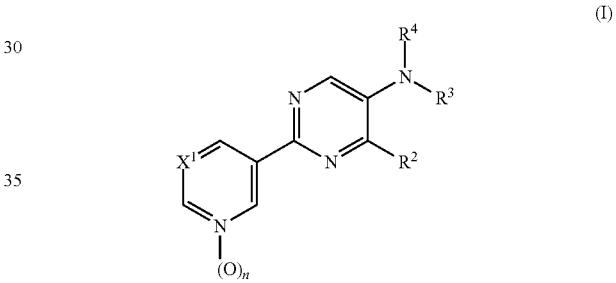

or a salt thereof, wherein:

$X^1$ is N or $CR^1$;

$R^1$ is selected from the group consisting of halogen, cyano, $C_1$-$C_6$alkyl, $C_3$-$C_6$cycloalkyl, $C_2$-$C_6$alkenyl, $C_2$-$C_6$alkynyl, $C_1$-$C_6$alkoxy, —C(O)OC$_1$-C$_6$alkyl, —S(O)$_p$C$_1$-C$_6$alkyl, NR$^6$R$^7$, $C_1$-$C_6$haloalkoxy and $C_1$-$C_6$haloalkyl;

$R^2$ is selected from the group consisting of halogen, cyano, nitro, $C_1$-$C_6$alkyl, $C_1$-$C_6$haloalkyl, $C_2$-$C_6$alkenyl, $C_2$-$C_6$alkynyl, $C_3$-$C_6$cycloalkyl, —C(O)OC$_1$-C$_6$alkyl, —S(O)$_p$(C$_1$-C$_6$alkyl), $C_1$-$C_6$alkoxy, $C_1$-$C_6$haloalkoxy and phenyl;

$R^3$ is selected from the group consisting of hydrogen, $C_1$-$C_6$alkyl, $C_2$-$C_6$alkenyl, $C_2$-$C_6$alkynyl, $C_2$-$C_6$haloalkenyl, $C_1$-$C_6$alkoxyC$_1$-$C_3$alkyl-, $C_1$-$C_6$haloalkyl- and —(CR$^a$R$^b$)$_q$R$^5$;

$R^a$ is hydrogen or $C_1$-$C_2$ alkyl;

$R^b$ is hydrogen or $C_1$-$C_2$ alkyl;

$R^4$ is selected from the group consisting of hydrogen, $C_1$-$C_6$alkyl, $C_2$-$C_6$alkenyl, $C_2$-$C_6$alkynyl, $C_2$-$C_6$haloalkenyl, $C_1$-$C_6$alkoxyC$_1$-$C_3$alkyl-, $C_1$-$C_6$haloalkyl- and —(CR$^a$R$^b$)$_q$R$^5$;

$R^5$ is —C(O)OC$_1$-C$_6$alkyl, —C$_3$-C$_{10}$cycloalkyl, -aryl and -heteroaryl wherein said aryl and heteroaryl are optionally substituted by 1 to 3 independent $R^8$;

or $R^3$ and $R^4$ together with the nitrogen to which they are attached, form a saturated or partially unsaturated 4-6 membered ring system optionally containing 1 or 2 further heteroatoms independently selected from S in the form $S(O)_p$, O and N, wherein said ring is optionally substituted by 1 to 3 $R^8$;

$R^6$ and $R^7$ are independently selected from the group consisting of hydrogen and $C_1$-$C_6$alkyl;

each $R^8$ is independently selected from the group consisting of halogen, $C_1$-$C_6$ alkyl and $C_1$-$C_6$alkoxy-, $C_1$-$C_6$ haloalkyl, $C_1$-$C_6$ haloalkoxy-, cyano and $S(O)_p(C_1$-$C_6$alkyl);

n is 0 or 1;

p is 0, 1, or 2; and q is 0, 1, or 2, and when q is 0, $R^5$ is not —C(O)O$C_1$-$C_6$aklyl;

with the proviso that the compound of formula (I) is not 2-(5-bromo-3-pyridyl)-4-methyl-pyrimidin-5-amine.

Compounds of formula (I) may exist as different geometric isomers, or in different tautomeric forms. This invention covers the use of all such isomers and tautomers, and mixtures thereof in all proportions, as well as isotopic forms such as deuterated compounds.

It may be the case that compounds of formula (I) may contain one or more asymmetric centers and may thus give rise to optical isomers and diastereomers. While shown without respect to stereochemistry, the present invention includes the use of all such optical isomers and diastereomers as well as the racemic and resolved, enantiomerically pure R and S stereoisomers and other mixtures of the R and S stereoisomers and agrochemically acceptable salts thereof.

Each alkyl moiety either alone or as part of a larger group (such as alkoxy, alkylthio, alkoxycarbonyl, alkylcarbonyl, alkylaminocarbonyl, or dialkylaminocarbonyl, et al.) may be straight-chained or branched. Typically, the alkyl is, for example, methyl, ethyl, n-propyl, isopropyl, n-butyl, sec-butyl, isobutyl, tert-butyl, n-pentyl, neopentyl, or n-hexyl. The alkyl groups are generally $C_1$-$C_6$ alkyl groups (except where already defined more narrowly), but are preferably $C_1$-$C_4$ alkyl or $C_1$-$C_3$ alkyl groups, and, more preferably, are $C_1$-$C_2$ alkyl groups (such as methyl).

Alkenyl and alkynyl moieties can be in the form of straight or branched chains, and the alkenyl moieties, where appropriate, can be of either the (E)- or (Z)-configuration. Alkenyl and alkynyl moieties can contain one or more double and/or triple bonds in any combination; but preferably contain only one double bond (for alkenyl) or only one triple bond (for alkynyl).

The alkenyl or alkynyl moieties are typically $C_2$-$C_4$ alkenyl or $C_2$-$C_4$ alkynyl, more specifically ethenyl (vinyl), prop-2-enyl, prop-3-enyl (allyl), ethynyl, prop-3-ynyl (propargyl), or prop-1-ynyl. Preferably, the term cycloalkyl refers to cyclopropyl, cyclobutyl, cyclopentyl or cyclohexyl.

In the context of the present specification the term "aryl" preferably means phenyl.

Heteroaryl groups and heteroaryl rings (either alone or as part of a larger group, such as heteroaryl-alkyl-) are ring systems containing at least one heteroatom and can be in mono- or bi-cyclic form. Preferably, single rings will contain 1, 2 or 3 ring heteroatoms selected independently from nitrogen, oxygen and sulfur. Typically "heteroaryl" is as used in the context of this invention includes furyl, thienyl, pyrrolyl, pyrazolyl, imidazolyl, triazolyl, oxazolyl, isoxazolyl, thiazolyl, isothiazolyl, oxadiazolyl, pyridyl, pyrimidinyl, pyridazinyl, pyrazinyl, and triazinyl rings, which may or may not be substituted as described herein.

Halogen (or halo) encompasses fluorine, chlorine, bromine or iodine. The same correspondingly applies to halogen in the context of other definitions, such as haloalkyl or halophenyl.

Haloalkyl groups having a chain length of from 1 to 6 carbon atoms are, for example, fluoromethyl, difluoromethyl, trifluoromethyl, chloromethyl, dichloromethyl, trichloromethyl, 2,2,2-trifluoroethyl, 2-fluoroethyl, 2-chloroethyl, pentafluoroethyl, 1,1-difluoro-2,2,2-trichloroethyl, 2,2,3,3-tetrafluoroethyl and 2,2,2-trichloroethyl, heptafluoro-n-propyl and perfluoro-n-hexyl.

Alkoxy groups preferably have a chain length of from 1 to 6 carbon atoms. Alkoxy is, for example, methoxy, ethoxy, propoxy, isopropoxy, n-butoxy, isobutoxy, sec-butoxy or tert-butoxy or a pentyloxy or hexyloxy isomer, preferably methoxy and ethoxy. It should also be appreciated that two alkoxy substituents may be present on the same carbon atom.

Haloalkoxy is, for example, fluoromethoxy, difluoromethoxy, trifluoromethoxy, 2,2,2-trifluoroethoxy, 1,1,2,2-tetrafluoroethoxy, 2-fluoroethoxy, 2-chloroethoxy, 2,2-difluoroethoxy or 2,2,2-trichloroethoxy, preferably difluoromethoxy, 2-chloroethoxy or trifluoromethoxy.

$C_1$-$C_6$ alkyl-S-(alkylthio) is, for example, methylthio, ethylthio, propylthio, isopropylthio, n-butylthio, isobutylthio, sec-butylthio or tert-butylthio, preferably methylthio or ethylthio.

$C_1$-$C_6$ alkyl-S(O)-(alkylsulfinyl) is, for example, methylsulfinyl, ethylsulfinyl, propylsulfinyl, isopropylsulfinyl, n-butylsulfinyl, isobutylsulfinyl, sec-butylsulfinyl or tert-butylsulfinyl, preferably methylsulfinyl or ethylsulfinyl.

$C_1$-$C_6$ alkyl-S(O)$_2$-(alkylsulfonyl) is, for example, methylsulfonyl, ethylsulfonyl, propylsulfonyl, isopropylsulfonyl, n-butylsulfonyl, isobutylsulfonyl, sec-butylsulfonyl or tert-butylsulfonyl, preferably methylsulfonyl or ethylsulfonyl.

Compounds of formula (I) may form, and/or be used as, agronomically acceptable salts with amines (for example ammonia, dimethylamine and triethylamine), alkali metal and alkaline earth metal bases or quaternary ammonium bases. Among the alkali metal and alkaline earth metal hydroxides, oxides, alkoxides and hydrogen carbonates and carbonates used in salt formation, emphasis is to be given to the hydroxides, alkoxides, oxides and carbonates of lithium, sodium, potassium, magnesium and calcium, but especially those of sodium, magnesium and calcium. The corresponding trimethylsulfonium salt may also be used.

Compounds of formula (I) may also form (and/or be used as) agronomically acceptable salts with various organic and/or inorganic acids, for example, acetic, propionic, lactic, citric, tartaric, succinic, fumaric, maleic, malonic, mandelic, malic, phthalic, hydrochloric, hydrobromic, phosphoric, nitric, sulfuric, methanesulfonic, naphthalenesulfonic, benzenesulfonic, toluenesulfonic, camphorsulfonic, and similarly known acceptable acids, when the compound of formula (I) contains a basic moiety.

Where appropriate compounds of formula (I) may also be in the form of/used as an N-oxide.

Compounds of formula (I) may also be in the form of/used as hydrates which may be formed during the salt formation.

Preferred values of $X^1$, $R^1$, $R^2$, $R^3$, $R^4$, $R^5$, $R^6$, $R^7$, $R^8$, n, p and q, are as set out below, and a compound of formula (I) according to the invention may comprise any combination of said values. The skilled person will appreciate that values for any specified set of embodiments may combined with values for any other set of embodiments where such combinations are not mutually exclusive.

In one particular embodiment of the present invention, $X^1$ is N.

In another embodiment of the present invention, $X^1$ is $CR^1$ and $R^1$ is preferably selected from the group consisting of cyano, fluoro, chloro, methoxy, difluoromethoxy and trifluoromethyl. More preferably still, $R^1$ is selected from the group consisting of cyano, fluoro, chloro, methoxy and trifluoromethyl. Even more preferably still, $R^1$ is cyano or fluoro.

Preferably $R^2$ is $C_1$-$C_6$alkyl, $C_1$-$C_6$haloalkyl, cyano, —C(O)O$C_1$-$C_6$alkyl, $C_1$-$C_6$alkoxy, or phenyl. More preferably $R^2$ is $C_1$-$C_6$alkyl, $C_1$-$C_6$haloalkyl, cyano —C(O)OCH$_3$, methoxy, or phenyl. Even more preferably $R^2$ is $C_1$-$C_4$alkyl or $C_1$-$C_4$haloalkyl. More preferably still $R^2$ is methyl or trifluoromethyl.

As stated above $R^3$ and $R^4$ are each independently selected from the group consisting of hydrogen, $C_1$-$C_6$alkyl, $C_2$-$C_6$alkenyl, $C_2$-$C_6$alkynyl, $C_2$-$C_6$haloalkenyl, $C_1$-$C_6$alkoxy$C_1$-$C_3$alkyl-, $C_1$-$C_6$haloalkyl- and —(CR$^a$R$^b$)$_q$R$^5$.

Where $R^3$ or $R^4$ is —(CR$^a$R$^b$)$_q$R$^5$, it is preferred in one set of embodiments that $R^5$ is phenyl or a 5-, or 6-membered heteroaryl ring optionally substituted as described herein.

More preferably $R^5$ is a phenyl, furyl, thienyl, pyrrolyl, pyrazolyl, imidazolyl, triazolyl, oxazolyl, isoxazolyl, thiazolyl, isothiazolyl, oxadiazolyl, pyridyl, pyrimidinyl, pyridazinyl, pyrazinyl, or triazinyl ring, optionally substituted by 1 to 3 $R^8$ as defined herein. More preferably still, $R^5$ is a phenyl, pyridyl, pyrimidinyl, pyridazinyl, pyrazinyl, or triazinyl ring, optionally substituted by 1 to 3 $R^8$. In one set of embodiments, $R^5$ is a phenyl ring, optionally substituted by 1-3 $R^8$, in particular where q is 0 or 1.

In preferred embodiments $R^3$ is selected from the group consisting of hydrogen, $C_1$-$C_6$alkyl, $C_2$-$C_6$alkenyl, $C_2$-$C_6$alkynyl, (CR$^a$R$^b$)$_q$R$^5$ (in particular where $R^5$ is as preferred below). More preferably $R^3$ is selected from the group consisting of hydrogen, $C_1$-$C_6$alkyl, $C_2$-$C_6$alkenyl, $C_2$-$C_6$alkynyl, phenyl, benzyl, —(CH$_2$)$C_3$-$C_{10}$cycloalkyl, —CH(CH$_3$)phenyl, —CH$_2$C(O)O$C_1$-$C_6$alkyl and —CH(CH$_3$)C(O)O$C_1$-$C_6$alkyl wherein said benzyl and phenyl are optionally substituted by one or more (preferably from one to three e.g. one, two or three) independent $R^8$. Even more preferably $R^3$ is selected from the group consisting of hydrogen, methyl, -allyl, -but-2-ynyl, —CH$_2$CO$_2$CH$_3$, —CH(CH$_3$)C(O)OCH$_3$, —(CH$_2$)-cPr, phenyl, benzyl and —CH(CH$_3$)phenyl wherein the benzyl and phenyl are optionally substituted by one or two substituents selected from the group consisting of —CF$_3$, F, Cl and MeO—. In one set of embodiments $R^3$ hydrogen, methyl, -allyl, -but-2-ynyl, preferably hydrogen, methyl, or allyl.

Preferably $R^4$ is hydrogen or $C_1$-$C_4$alkyl, more preferably hydrogen or methyl.

Preferably $R^5$ is $C_3$-$C_6$cycloalkyl, phenyl or a 5-10-membered heteroaryl ring system, optionally substituted as described herein. More preferably $R^5$ is a phenyl, furyl, thienyl, pyrrolyl, pyrazolyl, imidazolyl, triazolyl, oxazolyl, isoxazolyl, thiazolyl, isothiazolyl, oxadiazolyl, pyridyl, pyrimidinyl, pyridazinyl, pyrazinyl, pyrazolopyridinyl, or triazinyl ring system, optionally substituted by 1 to 3 $R^8$ as defined herein. In one set of embodiments $R^5$ is a phenyl, pyridyl, pyrimidinyl, pyridazinyl, pyrazinyl, or triazinyl ring, optionally substituted by 1 to 3 $R^8$, more preferably $R^5$ is a phenyl ring, optionally substituted by 1-3 $R^8$, in particular where q is 0 or 1. In a further set of embodiments, $R^5$ is a phenyl, thiazolyl, pyrazolyl, oxazolyl or pyrazolopyridinyl ring system optionally substituted by 1-3 $R^8$.

In one particular embodiment $R^6$ and $R^7$ are both hydrogen. In another embodiment $R^6$ is hydrogen and $R^7$ is $C_1$-$C_6$alkyl (e.g., methyl or ethyl). In another embodiment, $R^6$ and $R^7$ are both $C_1$-$C_6$alkyl.

In an alternative embodiment of the present invention, $R^3$ and $R^4$ together with the nitrogen atom to which they are joined, form a saturated or partially unsaturated 4-, 5-, or 6-membered ring system, preferably 5- or 6-membered, more preferably 6-membered, optionally containing from 1 or 2 further heteroatoms independently selected from S, O and N, wherein said ring is optionally substituted by 1 to 3 independent $R^8$. Examples of such ring systems include pyrrolinyl, pyrrolidinyl, pyrazolinyl, pyrazolidinyl, imidazolinyl, imidazolidinyl, triazolyl, piperidyl, morpholinyl, thiomorpholinyl, and piperazinyl rings. Preferably in such embodiments, $R^3$ and $R^4$ together with the nitrogen atom to which they are joined form a pyrrolidinyl, piperidyl, morpholinyl, thiomorpholinyl, or piperazinyl ring.

As stated above, each $R^8$ is independently selected from the group consisting of halogen, $C_1$-$C_6$ alkyl and $C_1$-$C_6$alkoxy-, $C_1$-$C_6$ haloalkyl, $C_1$-$C_6$ haloalkoxy-, cyano and S(O)$_p$($C_1$-$C_6$alkyl). Preferably each $R^8$ is independently halogen, $C_1$-$C_6$ alkyl, $C_1$-$C_6$ haloalkyl or $C_1$-$C_6$ alkoxy. More preferably each $R^8$ is independently fluoro, chloro, methyl, trifluoromethyl or methoxy.

Table 1 below provides 15 specific examples of herbicidal compounds of Formula (I) for use according to the invention.

TABLE 1

Specific examples of compounds of Formula (I) for use in the invention wherein $X^1$, $R^2$, $R^3$ and $R^4$ are as shown below in the table

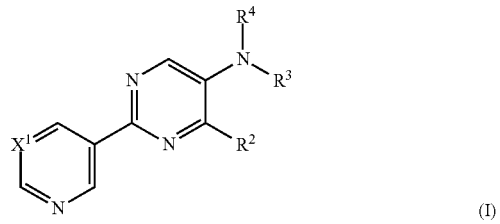

(I)

| Compound ID | $X^1$ | $R^2$ | $R^3$ | $R^4$ |
|---|---|---|---|---|
| D1 | C—F | CH$_3$ | CH$_3$ | H |
| D2 | C—F | CH$_3$ | H | H |
| D3 | N | CH$_3$ | H | H |
| D4 | N | CH$_3$ | CH$_3$ | H |
| D5 | C—F | CH$_3$ | H | H |
| D6 | C—F | CH$_3$ | CH$_3$ | H |
| D7 | N | CH$_3$ | CH$_2$CH=CH$_2$ | H |
| D8 | C—F | CH$_3$ | CH$_3$ | CH$_3$ |
| D9 | N | CH$_3$ | H | H |
| D10 | C—CN | CH$_3$ | H | H |
| D11 | C—F | CH$_3$ | CH$_2$CH$_3$ | H |
| D12 | C—F | CH$_3$ | CH$_2$CH$_3$ | CH$_2$CH$_3$ |
| D13 | C—F | CH$_3$ | CH$_2$CH$_2$CH$_3$ | H |
| D14 | C—F | CH$_3$ | CH$_2$CH$_2$CH$_3$ | CH2CH$_2$CH$_3$ |
| D15 | C—F | CH$_3$ | 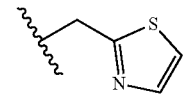 [SMILES: *Cc1nccs1] | H |

Compounds of Formula (I) may be prepared according to the following schemes, in which the substituents $X^1$, $R^1$, $R^2$, $R^3$, $R^4$, $R^5$, $R^6$, $R^7$, $R^8$, $R^a$, $R^b$, n, p and q have (unless otherwise stated explicitly) the definitions described hereinbefore, using techniques known to the person skilled in the art of organic chemistry. General methods for the production of compounds of formula (I) are described below. The starting materials used for the preparation of the compounds of the invention may be purchased from the usual commercial suppliers or may be prepared by known methods. The starting materials as well as the intermediates may be purified before use in the next step by state of the art methodologies such as chromatography, crystallization, distillation and filtration.

Typical abbreviations used throughout are as follows:
app=apparent
Br. or br=broad
$^tBu$=tert-butyl
t-BuOH=tert-butanol
d=doublet
dd=double doublet
Dba=dibenzylideneacetone
DCM=dichloromethane
DMF=N, N-dimethylformamide
DMSO=dimethylsulfoxide
DPPA=diphenylphosphoryl azide
Et=ethyl
$Et_3N$=triethylamine
$Et_2O$=diethyl ether
EtOAc=ethyl acetate
EtOH=ethanol
HPLC=high performance liquid chromatography
m=multiplet
mCPBA=meta-chloro-perbenzoic acid
Me=methyl
MeOH=methanol
Ms=mesylate
NaOEt=sodium ethoxide
NMR=nuclear magnetic resonance
Ph=phenyl
q=quartet
RT=room temperature
s=singlet
t=triplet
Tf=triflate
TFA=trifluoroacetic acid
THF=tetrahydrofuran
TMS=tetramethylsilane
rt=retention time.

Processes for preparation of compounds, e.g. a compound of formula (I) (which optionally can be an agrochemically acceptable salt thereof), are now described, and form further aspects of the present invention.

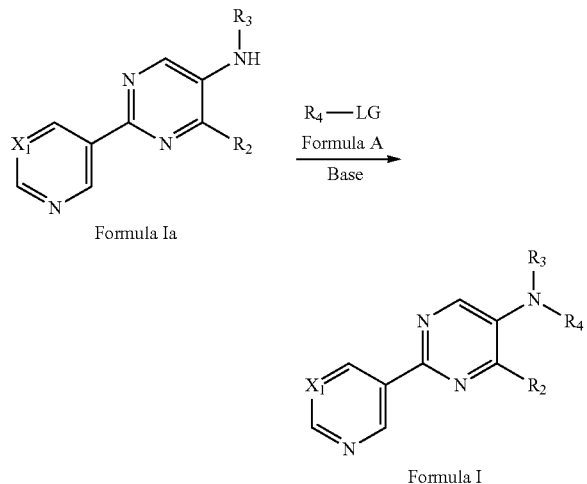

A compound of Formula (I) (where either $R^3$ and/or $R^4 \neq H$) can be prepared from a compound of Formula Ia via an alkylation reaction with a compound of Formula A (where LG is a suitable leaving group, such as Br, I or OMs) in the presence of a suitable base and in a suitable solvent. Suitable bases include. Compounds of Formula A are commercially available or can be prepared by methods well known in the literature.

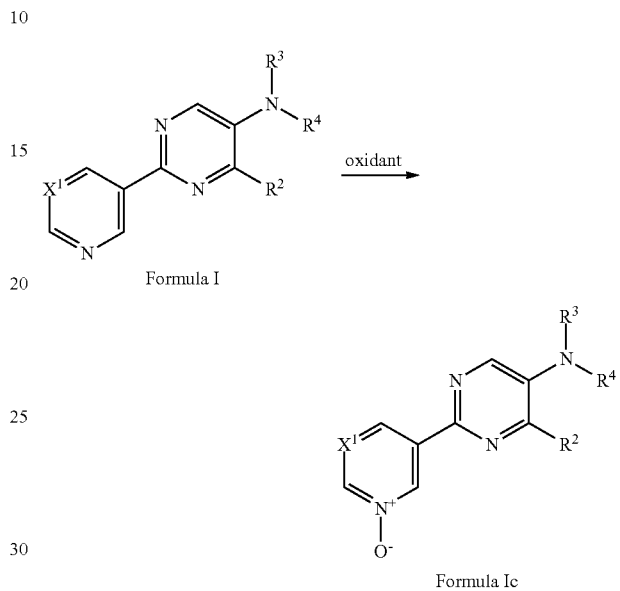

A compound of Formula Ic (a compound of Formula (I) where n is 1) may be prepared from a compound of Formula I (where n is 0) via reaction with a suitable oxidant in a suitable solvent. Suitable oxidants may include 3-chloroperbenzoic acid. Suitable solvents may include DCM.

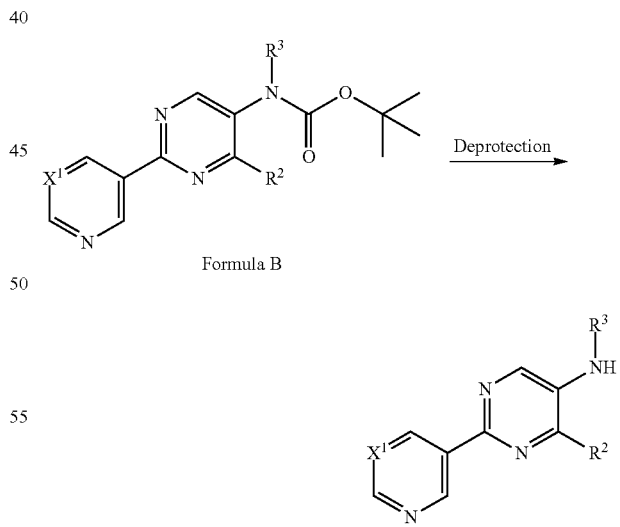

A compound of Formula Ia (i.e. a compound of Formula (I) where $R^4$ is hydrogen) may be prepared from a compound of Formula B via a deprotection reaction using a suitable reagent in a suitable solvent. Suitable reagents may include trifluoroacetic acid. Suitable solvents may include DCM.

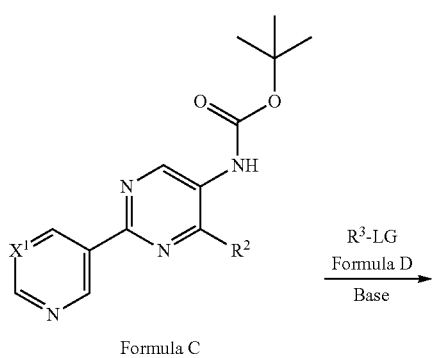

Formula C

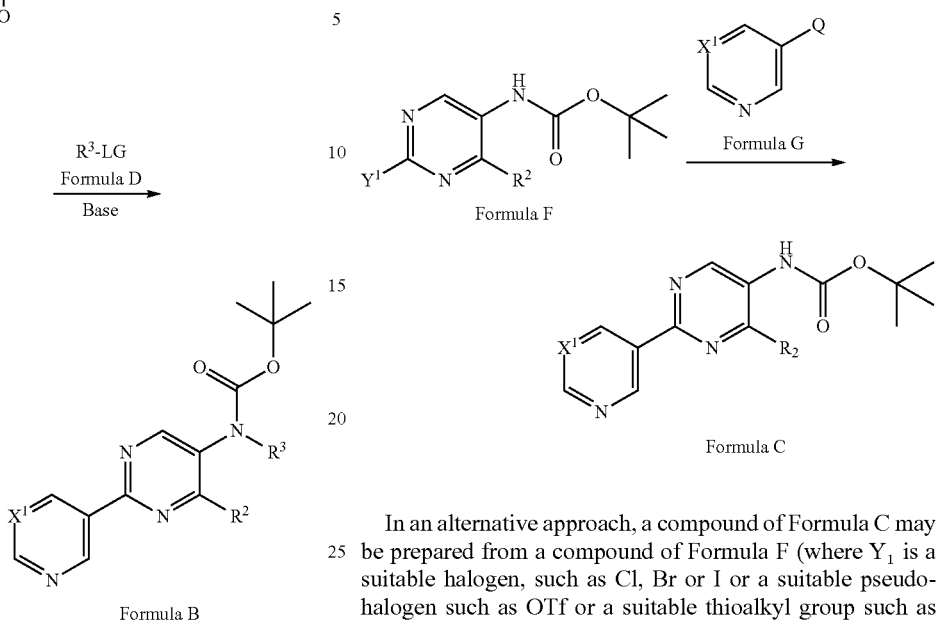

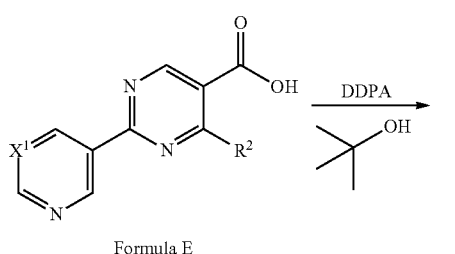

Formula B

A compound of Formula B may be prepared from a compound of Formula C via reaction with a compound of Formula D (where LG is a suitable leaving group, such as Br, I or OMs) in the presence of a suitable base and in a suitable solvent. Suitable bases may include sodium hydride. Suitable solvents may include DMF or THF. Compounds of Formula D are commercially available or can be prepared by methods well known in the literature.

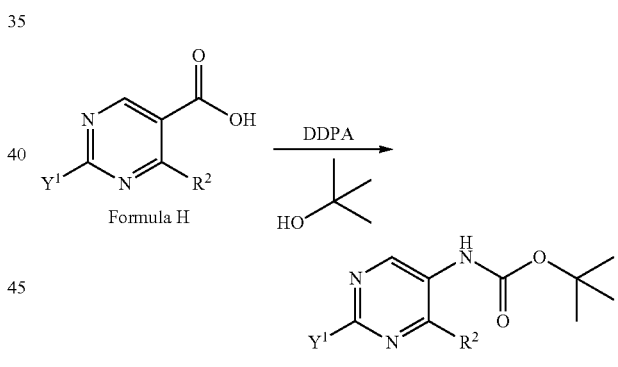

Formula E

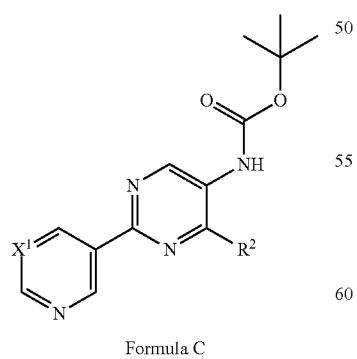

Formula C

A compound of Formula C may be prepared from a compound of Formula E via a Curtius reaction in the presence of a suitable reagent and in the presence of tert-butanol and in a suitable solvent. Suitable reagents may include DPPA. Suitable solvents may include toluene.

In an alternative approach, a compound of Formula C may be prepared from a compound of Formula F (where $Y_1$ is a suitable halogen, such as Cl, Br or I or a suitable pseudo-halogen such as OTf or a suitable thioalkyl group such as SMe) with a compound of Formula G (where Q is a suitable coupling group, such as —B(OH)$_2$ or —B(OR)$_2$ or —SnR$_3$) in the presence of a suitable catalyst, optionally in the presence of a suitable base and in a suitable solvent. Compounds of Formula G are commercially available or can be prepared by methods well known in the literature.

A compound of Formula F may be prepared from a compound of Formula H via a Curtius reaction in the presence of a suitable reagent and in the presence of tert-butanol and in a suitable solvent. Suitable reagents may include DPPA. Suitable solvents may include toluene.

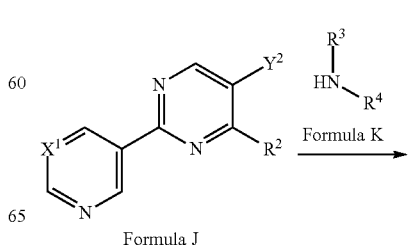

Formula J

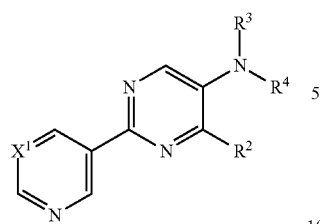

Formula I

In an alternative approach, a compound of Formula (I) may be prepared from a compound of Formula J (where $Y_2$ is a suitable halogen, such as Cl, Br or I or suitable pseudohalogen, such as OTf) via reaction with a compound of Formula K, optionally in the presence of a suitable catalyst, optionally in the presence of a suitable ligand and optionally in the presence of a suitable base and in a suitable solvent. Compounds of Formula K are commercially available or can be prepared by methods well known in the literature.

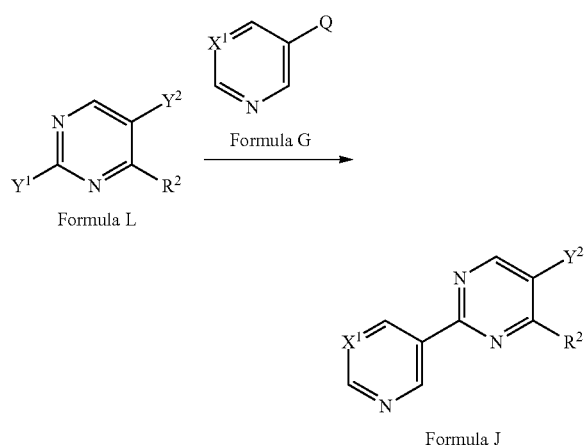

A compound of Formula J may be prepared from a compound of Formula L (where $Y_1$ is a suitable halogen, such as Cl, Br or I or a suitable pseudohalogen, such as OTf) via a cross-coupling reaction with a compound of Formula G (where Q is a suitable coupling group, such as —B(OH)$_2$ or —B(OR)$_2$ or —SnR$_3$) in the presence of a suitable catalyst, optionally in the presence of a suitable base and in a suitable solvent. Compounds of Formula L and of Formula G are commercially available or can be prepared by methods well known in the literature.

Formula I

In a further alternative approach, a compound of Formula (I) may be prepared from a compound of Formula M (where $Y_1$ is a suitable halogen, such as Cl, Br or I or a suitable pseudohalogen, such as OTf) via a cross-coupling reaction with a compound of Formula G (where Q is a suitable coupling group, such as —B(OH)$_2$ or —B(OR)$_2$ or —SnR$_3$) in the presence of a suitable catalyst, optionally in the presence of a suitable base and in a suitable solvent. Compounds of Formula G are commercially available or can be prepared by methods well known in the literature.

A compound of Formula M may be prepared from a compound of Formula L (where $Y^2$ is a suitable halogen, such as Br or I or suitable pseudohalogen, such as OTf) via reaction with a compound of Formula K, optionally in the presence of a suitable catalyst and optionally in the presence of a suitable base and in a suitable solvent. Compounds of Formula L and of Formula K are commercially available or can be prepared by methods well known in the literature.

A compound of Formula Ia where $R^3$ is not hydrogen may be prepared from a compound of Formula Ib via a reductive amination reaction with a compound of a compound of Formula N in the presence of a suitable reducing agent and in a suitable solvent. Suitable solvents include ethanol or methanol. Compounds of Formula N are commercially available or can be prepared by methods well known in the literature.

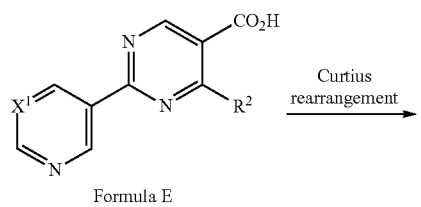

Formula E

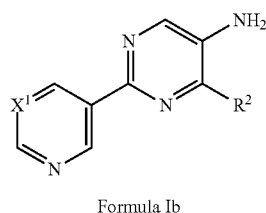

Formula Ib

In an alternative approach, a compound of Formula Ib may be prepared from a compound of Formula E via a Curtius rearrangement using a suitable reagent in a suitable solvent. Suitable reagents include DPPA and suitable solvents include DMF or toluene.

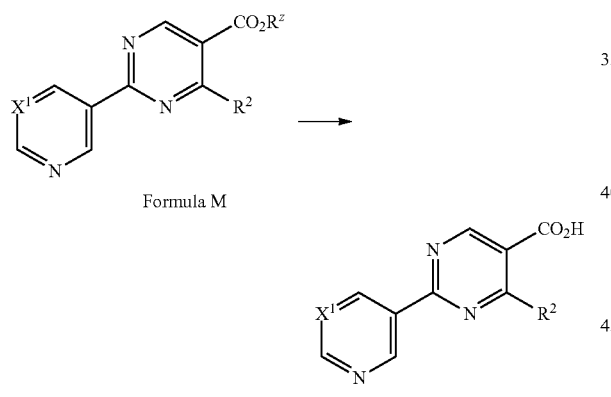

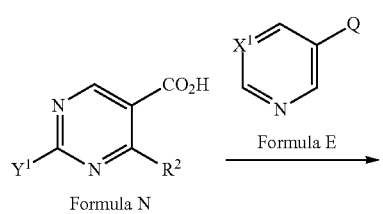

Formula N

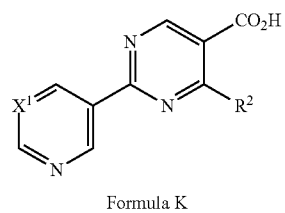

Formula K

In an alternative approach, a compound of Formula K may be prepared from a compound of Formula N (where $Y^1$ is a suitable halogen, such as Cl, Br or I or suitable pseudohalogen, such as OTf) via a cross-coupling reaction with a compound of Formula E (where Q is a suitable coupling group, such as —B(OH)$_2$ or —B(OR)$_2$ or —SnR$_3$) in the presence of a suitable catalyst, optionally in the presence of a suitable base and in a suitable solvent. Suitable catalysts may include Pd(PPh$_3$)$_4$ or [1,1'-bis(diphenylphosphino)ferrocene]dichloropalladium(II). Suitable bases may include K$_2$CO$_3$, Na$_2$CO$_3$, Cs$_2$CO$_3$, K$_3$PO$_4$ or CsF. Suitable solvents may include ethylene glycol dimethyl ether, acetonitrile, DMF, ethanol, 1,4-dioxane, tetrahydrofuran and/or water. Compounds of Formula E are commercially available or can be prepared by methods well known in the literature.

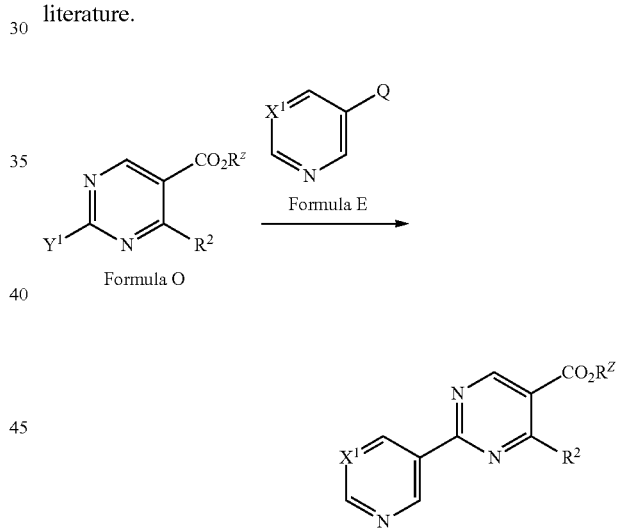

A compound of Formula M may be prepared from a compound of Formula O where $Y_1$ is a suitable halogen(such as Cl, Br or) or suitable pseudohalogen (such as OTf) via a cross-coupling reaction with a compound of Formula E (where Q is a suitable coupling group, such as —B(OH)$_2$ or —B(OR)$_2$ or —SnR$_3$) in the presence of a suitable catalyst, optionally in the presence of a suitable base and in a suitable solvent. Suitable catalysts may include Pd(PPh$_3$)$_4$ or [1,1'-bis(diphenylphosphino)ferrocene]dichloropalladium(II).
Suitable bases may include K$_2$CO$_3$, Na$_2$CO$_3$, Cs$_2$CO$_3$, K$_3$PO$_4$ or CsF. Suitable solvents may include ethylene glycol dimethyl ether, acetonitrile, DMF, ethanol, 1,4-dioxane, tetrahydrofuran and/or water. Compounds of Formula E are commercially available or can be prepared by methods well known in the literature.

A compound of Formula K may be prepared from a compound of Formula M (where $R^z$=C$_{1-6}$ alkyl) via a hydrolysis reaction in the presence of a suitable reagent in a suitable solvent. Suitable reagents include NaOH, LiOH or KOH. Suitable solvents include H$_2$O, THF, MeOH or EtOH or mixtures thereof.

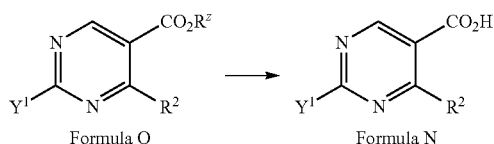

Formula O       Formula N

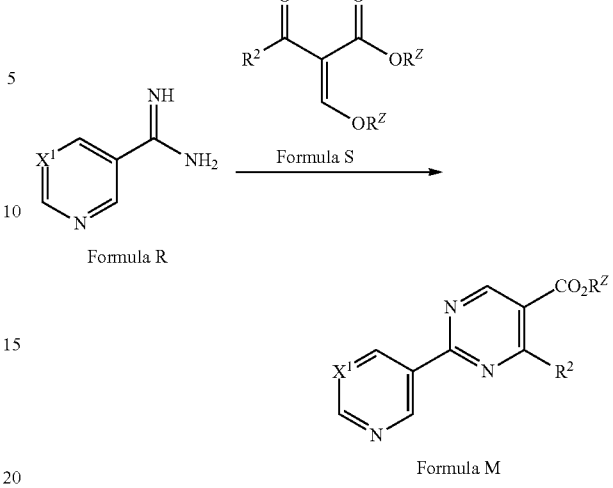

Formula R       Formula S

Formula M

A compound of Formula N may be prepared from a compound of Formula O where $R^z$ is $C_{1-6}$ alkyl via an ester hydrolysis reaction in the presence of a suitable reagent in a suitable solvent. Suitable reagents may include NaOH, LiOH or tetra(n-butyl) ammonium hydroxide. Suitable solvents may include $H_2O$, THF, MeOH, EtOH or combinations thereof.

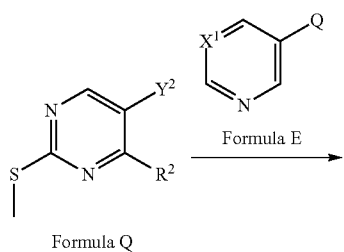

Formula Q       Formula E

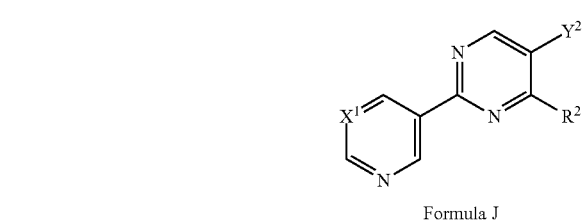

Formula J

In a yet further alternative approach, a compound of Formula M may be prepared from a compound of Formula R via a cyclisation reaction with a compound of Formula S in the presence of a suitable base and in a suitable solvent. Suitable bases may include NaOEt. Suitable solvents may include EtOH. Compounds of Formula S and of Formula R may be prepared by methods well known in the literature.

The compounds of Formula (I) as described herein may be used as herbicides by themselves, but they are generally formulated into herbicidal compositions using formulation adjuvants, such as carriers, solvents and surface-active agents (SFAs). Thus, the present invention further provides a herbicidal composition comprising a herbicidal compound as described herein and an agriculturally acceptable formulation adjuvant. The composition can be in the form of concentrates which are diluted prior to use, although ready-to-use compositions can also be made. The final dilution is usually made with water, but can be made instead of, or in addition to, water, with, for example, liquid fertilisers, micronutrients, biological organisms, oil or solvents.

In an alternative approach, a compound of Formula J may be prepared from a compound of Formula Q via a cross-coupling reaction (known as a Liebeskind-Srogl coupling) with a compound of Formula E (where Q is a suitable coupling group, such as —$B(OH)_2$) in the presence of a suitable catalyst, a suitable ligand, a suitable co-catalyst and in a suitable solvent. Suitable catalysts may include tris(dibenzylideneacetone)dipalladium(0), suitable ligands may include tris(2-furyl)phosphane, suitable co-catalysts may include copper(I) 3-methylsalicylate and suitable solvents may include THF. Compounds of Formula E are commercially available or can be prepared by methods well known in the literature.

Such herbicidal compositions generally comprise from 0.1 to 99% by weight, especially from 0.1 to 95% by weight of compounds of Formula (I) and from 1 to 99.9% by weight of a formulation adjuvant, which preferably includes from 0 to 25% by weight of a surface-active substance.

The compositions can be chosen from a number of formulation types, many of which are known from the Manual on Development and Use of FAO Specifications for Plant Protection Products, 5th Edition, 1999. These include dustable powders (DP), soluble powders (SP), water soluble granules (SG), water dispersible granules (WG), wettable powders (WP), granules (GR) (slow or fast release), soluble concentrates (SL), oil miscible liquids (OL), ultra low volume liquids (UL), emulsifiable concentrates (EC), dispersible concentrates (DC), emulsions (both oil in water (EW) and water in oil (EO)), micro-emulsions (ME), suspension concentrates (SC), aerosols, capsule suspensions (CS) and seed treatment formulations. The formulation type chosen in any instance will depend upon the particular purpose envisaged and the physical, chemical and biological properties of the compound of Formula (I).

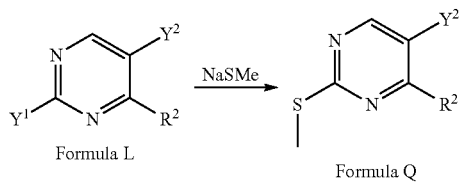

Formula L       Formula Q

A compound of Formula Q may be prepared from a compound of Formula L (where $Y^1$ is a suitable halogen, such as Cl) via a displacement reaction with NaSMe in a suitable solvent. Suitable solvents may include MeOH.

Dustable powders (DP) may be prepared by mixing a compound of Formula (I) with one or more solid diluents (for example natural clays, kaolin, pyrophyllite, bentonite, alumina, montmorillonite, kieselguhr, chalk, diatomaceous earths, calcium phosphates, calcium and magnesium carbonates, sulphur, lime, flours, talc and other organic and inorganic solid carriers) and mechanically grinding the mixture to a fine powder.

Soluble powders (SP) may be prepared by mixing a compound of Formula (I) with one or more water-soluble inorganic salts (such as sodium bicarbonate, sodium carbonate or magnesium sulphate) or one or more water-soluble organic solids (such as a polysaccharide) and, optionally, one or more wetting agents, one or more dispersing agents or a mixture of said agents to improve water dispersibility/solubility. The mixture is then ground to a fine powder. Similar compositions may also be granulated to form water soluble granules (SG).

Wettable powders (WP) may be prepared by mixing a compound of Formula (I) with one or more solid diluents or carriers, one or more wetting agents and, preferably, one or more dispersing agents and, optionally, one or more suspending agents to facilitate the dispersion in liquids. The mixture is then ground to a fine powder. Similar compositions may also be granulated to form water dispersible granules (WG).

Granules (GR) may be formed either by granulating a mixture of a compound of Formula (I) and one or more powdered solid diluents or carriers, or from pre-formed blank granules by absorbing a compound of Formula (I) (or a solution thereof, in a suitable agent) in a porous granular material (such as pumice, attapulgite clays, fuller's earth, kieselguhr, diatomaceous earths or ground corn cobs) or by adsorbing a compound of Formula (I) (or a solution thereof, in a suitable agent) on to a hard core material (such as sands, silicates, mineral carbonates, sulphates or phosphates) and drying if necessary. Agents which are commonly used to aid absorption or adsorption include solvents (such as aliphatic and aromatic petroleum solvents, alcohols, ethers, ketones and esters) and sticking agents (such as polyvinyl acetates, polyvinyl alcohols, dextrins, sugars and vegetable oils). One or more other additives may also be included in granules (for example an emulsifying agent, wetting agent or dispersing agent).

Dispersible Concentrates (DC) may be prepared by dissolving a compound of Formula (I) in water or an organic solvent, such as a ketone, alcohol or glycol ether. These solutions may contain a surface active agent (for example to improve water dilution or prevent crystallisation in a spray tank).

Emulsifiable concentrates (EC) or oil-in-water emulsions (EW) may be prepared by dissolving a compound of Formula (I) in an organic solvent (optionally containing one or more wetting agents, one or more emulsifying agents or a mixture of said agents).

Suitable organic solvents for use in ECs include aromatic hydrocarbons (such as alkylbenzenes or alkylnaphthalenes, exemplified by SOLVESSO 100, SOLVESSO 150 and SOLVESSO 200; SOLVESSO is a Registered Trade Mark), ketones (such as cyclohexanone or methylcyclohexanone) and alcohols (such as benzyl alcohol, furfuryl alcohol or butanol), N-alkylpyrrolidones (such as N-methylpyrrolidone or N-octylpyrrolidone), dimethyl amides of fatty acids (such as $C_8$-$C_{10}$ fatty acid dimethylamide) and chlorinated hydrocarbons. An EC product may spontaneously emulsify on addition to water, to produce an emulsion with sufficient stability to allow spray application through appropriate equipment.

Preparation of an EW involves obtaining a compound of Formula (I) either as a liquid (if it is not a liquid at room temperature, it may be melted at a reasonable temperature, typically below 70° C.) or in solution (by dissolving it in an appropriate solvent) and then emulsifying the resultant liquid or solution into water containing one or more SFAs, under high shear, to produce an emulsion. Suitable solvents for use in EWs include vegetable oils, chlorinated hydrocarbons (such as chlorobenzenes), aromatic solvents (such as alkylbenzenes or alkylnaphthalenes) and other appropriate organic solvents which have a low solubility in water.

Microemulsions (ME) may be prepared by mixing water with a blend of one or more solvents with one or more SFAs, to produce spontaneously a thermodynamically stable isotropic liquid formulation. A compound of Formula (I) is present initially in either the water or the solvent/SFA blend. Suitable solvents for use in MEs include those hereinbefore described for use in in ECs or in EWs. An ME may be either an oil-in-water or a water-in-oil system (which system is present may be determined by conductivity measurements) and may be suitable for mixing water-soluble and oil-soluble pesticides in the same formulation. An ME is suitable for dilution into water, either remaining as a microemulsion or forming a conventional oil-in-water emulsion.

Suspension concentrates (SC) may comprise aqueous or non-aqueous suspensions of finely divided insoluble solid particles of a compound of Formula (I). SCs may be prepared by ball or bead milling the solid compound of Formula (I) in a suitable medium, optionally with one or more dispersing agents, to produce a fine particle suspension of the compound. One or more wetting agents may be included in the composition and a suspending agent may be included to reduce the rate at which the particles settle. Alternatively, a compound of Formula (I) may be dry milled and added to water, containing agents hereinbefore described, to produce the desired end product.

Aerosol formulations comprise a compound of Formula (I) and a suitable propellant (for example n-butane). A compound of Formula (I) may also be dissolved or dispersed in a suitable medium (for example water or a water miscible liquid, such as n-propanol) to provide compositions for use in non-pressurised, hand-actuated spray pumps.

Capsule suspensions (CS) may be prepared in a manner similar to the preparation of EW formulations but with an additional polymerisation stage such that an aqueous dispersion of oil droplets is obtained, in which each oil droplet is encapsulated by a polymeric shell and contains a compound of Formula (I) and, optionally, a carrier or diluent therefor. The polymeric shell may be produced by either an interfacial polycondensation reaction or by a coacervation procedure. The compositions may provide for controlled release of the compound of Formula (I) and they may be used for seed treatment. A compound of Formula (I) may also be formulated in a biodegradable polymeric matrix to provide a slow, controlled release of the compound.

The composition may include one or more additives to improve the biological performance of the composition, for example by improving wetting, retention or distribution on surfaces; resistance to rain on treated surfaces; or uptake or mobility of a compound of Formula (I). Such additives include surface active agents (SFAs), spray additives based on oils, for example certain mineral oils or natural plant oils (such as soy bean and rape seed oil), and blends of these with other bio-enhancing adjuvants (ingredients which may aid or modify the action of a compound of Formula (I)).

Wetting agents, dispersing agents and emulsifying agents may be SFAs of the cationic, anionic, amphoteric or non-ionic type.

Suitable SFAs of the cationic type include quaternary ammonium compounds (for example cetyltrimethyl ammonium bromide), imidazolines and amine salts.

Suitable anionic SFAs include alkali metals salts of fatty acids, salts of aliphatic monoesters of sulphuric acid (for example sodium lauryl sulphate), salts of sulphonated aromatic compounds (for example sodium dodecylbenzenesulphonate, calcium dodecylbenzenesulphonate, butylnaphthalene sulphonate and mixtures of sodium di-isopropyl- and tri-isopropyl-naphthalene sulphonates), ether sulphates, alcohol ether sulphates (for example sodium laureth-3-sulphate), ether carboxylates (for example sodium laureth-3-carboxylate), phosphate esters (products from the reaction between one or more fatty alcohols and phosphoric acid (predominately mono-esters) or phosphorus pentoxide (predominately di-esters), for example the reaction between lauryl alcohol and tetraphosphoric acid; additionally these products may be ethoxylated), sulphosuccinamates, paraffin or olefine sulphonates, taurates and lignosulphonates.

Suitable SFAs of the amphoteric type include betaines, propionates and glycinates.

Suitable SFAs of the non-ionic type include condensation products of alkylene oxides, such as ethylene oxide, propylene oxide, butylene oxide or mixtures thereof, with fatty alcohols (such as oleyl alcohol or cetyl alcohol) or with alkylphenols (such as octylphenol, nonylphenol or octylcresol); partial esters derived from long chain fatty acids or hexitol anhydrides; condensation products of said partial esters with ethylene oxide; block polymers (comprising ethylene oxide and propylene oxide); alkanolamides; simple esters (for example fatty acid polyethylene glycol esters); amine oxides (for example lauryl dimethyl amine oxide); and lecithins.

Suitable suspending agents include hydrophilic colloids (such as polysaccharides, polyvinylpyrrolidone or sodium carboxymethylcellulose) and swelling clays (such as bentonite or attapulgite).

Herbicidal compositions as described herein may further comprise at least one additional pesticide. For example, the compounds of formula (I) can also be used in combination with other herbicides or plant growth regulators. In a preferred embodiment the additional pesticide is a herbicide or herbicide safener. Examples of such mixtures are, in which 'I' represents a compound of Formula (I), I+acetochlor, I+acifluorfen, I+acifluorfen-sodium, I+aclonifen, I+acrolein, I+alachlor, I+alloxydim, I+ametryn, I+amicarbazone, I+amidosulfuron, I+aminopyralid, I+amitrole, I+anilofos, I+asulam, I+atrazine, I+azafenidin, I+azimsulfuron, I+BCPC, I+beflubutamid, I+benazolin, I+bencarbazone, I+benfluralin, I+benfuresate, I+bensulfuron, I+bensulfuron-methyl, I+bensulide, I+bentazone, I+benzfendizone, I+benzobicyclon, I+benzofenap, I+bicyclopyrone, I+bifenox, I+bilanafos, I+bispyribac, I+bispyribac-sodium, I+borax, I+bromacil, I+bromobutide, I+bromoxynil, I+butachlor, I+butamifos, I+butralin, I+butroxydim, I+butylate, I+cacodylic acid, I+calcium chlorate, I+cafenstrole, I+carbetamide, I+carfentrazone, I+carfentrazone-ethyl, I+chlorflurenol, I+chlorflurenol-methyl, I+chloridazon, I+chlorimuron, I+chlorimuron-ethyl, I+chloroacetic acid, I+chlorotoluron, I+chlorpropham, I+chlorsulfuron, I+chlorthal, I+chlorthaldimethyl, I+cinidon-ethyl, I+cinmethylin, I+cinosulfuron, I+cisanilide, I+clethodim, I+clodinafop, I+clodinafop-propargyl, I+clomazone, I+clomeprop, I+clopyralid, I+cloransulam, I+cloransulam-methyl, I+cyanazine, I+cycloate, I+cyclosulfamuron, I+cycloxydim, I+cyhalofop, I+cyhalofop-butyl, I+2,4-D, I+daimuron, I+dalapon, I+dazomet, I+2,4-DB, I+I+desmedipham, I+dicamba, I+dichlobenil, I+dichlorprop, I+dichlorprop-P, I+diclofop, I+diclofop-methyl, I+diclosulam, I+difenzoquat, I+difenzoquat metilsulfate, I+diflufenican, I+diflufenzopyr, I+dimefuron, I+dimepiperate, I+dimethachlor, I+dimethametryn, I+dimethenamid, I+dimethenamid-P, I+dimethipin, I+dimethylarsinic acid, I+dinitramine, I+dinoterb, I+diphenamid, I+dipropetryn, I+diquat, I+diquat dibromide, I+dithiopyr, I+diuron, I+endothal, I+EPTC, I+esprocarb, I+ethalfluralin, I+ethametsulfuron, I+ethametsulfuron-methyl, I+ethephon, I+ethofumesate, I+ethoxyfen, I+ethoxysulfuron, I+etobenzanid, I+fenoxaprop-P, I+fenoxaprop-P-ethyl, I+fentrazamide, I+ferrous sulfate, I+flamprop-M, I+flazasulfuron, I+florasulam, I+fluazifop, I+fluazifop-butyl, I+fluazifop-P, I+fluazifop-P-butyl, I+fluazolate, I+flucarbazone, I+flucarbazone-sodium, I+flucetosulfuron, I+fluchloralin, I+flufenacet, I+flufenpyr, I+flufenpyr-ethyl, I+flumetralin, I+flumetsulam, I+flumiclorac, I+flumiclorac-pentyl, I+flumioxazin, I+flumipropin, I+fluometuron, I+fluoroglycofen, I+fluoroglycofen-ethyl, I+fluoxaprop, I+flupoxam, I+flupropacil, I+flupropanate, I+flupyrsulfuron, I+flupyrsulfuron-methyl-sodium, I+flurenol, I+fluridone, I+flurochloridone, I+fluroxypyr, I+flurtamone, I+fluthiacet, I+fluthiacet-methyl, I+fomesafen, I+foramsulfuron, I+fosamine, I+glufosinate, I+glufosinate-ammonium, I+glyphosate, I+halauxifen, I+halosulfuron, I+halosulfuron-methyl, I+haloxyfop, I+haloxyfop-P, I+hexazinone, I+imazamethabenz, I+imazamethabenz-methyl, I+imazamox, I+imazapic, I+imazapyr, I+imazaquin, I+imazethapyr, I+imazosulfuron, I+indanofan, I+indaziflam, I+iodomethane, I+iodosulfuron, I+iodosulfuron-methyl-sodium, I+ioxynil, I+isoproturon, I+isouron, I+isoxaben, I+isoxachlortole, I+isoxaflutole, I+isoxapyrifop, I+karbutilate, I+lactofen, I+lenacil, I+linuron, I+mecoprop, I+mecoprop-P, I+mefenacet, I+mefluidide, I+mesosulfuron, I+mesosulfuron-methyl, I+mesotrione, I+metam, I+metamifop, I+metamitron, I+metazachlor, I+methabenzthiazuron, I+methazole, I+methylarsonic acid, I+methyldymron, I+methyl isothiocyanate, I+metolachlor, I+S-metolachlor, I+metosulam, I+metoxuron, I+metribuzin, I+metsulfuron, I+metsulfuron-methyl, I+molinate, I+monolinuron, I+naproanilide, I+napropamide, I+naptalam, I+neburon, I+nicosulfuron, I+n-methyl glyphosate, I+nonanoic acid, I+norflurazon, I+oleic acid (fatty acids), I+orbencarb, I+orthosulfamuron, I+oryzalin, I+oxadiargyl, I+oxadiazon, I+oxasulfuron, I+oxaziclomefone, I+oxyfluorfen, I+paraquat, I+paraquat dichloride, I+pebulate, I+pendimethalin, I+penoxsulam, I+pentachlorophenol, I+pentanochlor, I+pentoxazone, I+pethoxamid, I+phenmedipham, I+picloram, I+picolinafen, I+pinoxaden, I+piperophos, I+pretilachlor, I+primisulfuron, I+primisulfuron-methyl, I+prodiamine, I+profoxydim, I+prohexadione-calcium, I+prometon, I+prometryn, I+propachlor, I+propanil, I+propaquizafop, I+propazine, I+propham, I+propisochlor, I+propoxycarbazone, I+propoxycarbazone-sodium, I+propyzamide, I+prosulfocarb, I+prosulfuron, I+pyraclonil, I+pyraflufen, I+pyraflufen-ethyl, I+pyrasulfotole, I+pyrazolynate, I+pyrazosulfuron, I+pyrazosulfuron-ethyl, I+pyrazoxyfen, I+pyribenzoxim, I+pyributicarb, I+pyridafol, I+pyridate, I+pyriftalid, I+pyriminobac, I+pyriminobac-methyl, I+pyrimisulfan, I+pyrithiobac, I+pyrithiobac-sodium, I+pyroxasulfone, I+pyroxsulam, I+quinclorac, I+quinmerac, I+quinoclamine, I+quizalofop, I+quizalofop-P, I+rimsulfuron, I+saflufenacil, I+sethoxydim, I+siduron, I+simazine, I+simetryn, I+sodium chlorate, I+sulcotrione, I+sulfentrazone, I+sulfometuron, I+sulfometuron-methyl, I+sulfosate, I+sulfosulfuron, I+sulfuric acid, I+tebuthiuron, I+tefuryltrione, I+tembotrione, I+tepraloxydim, I+terbacil, I+terbumeton, I+terbuthylazine, I+terbutryn, I+thenylchlor, I+thiazopyr, I+thifensulfuron, I+thiencarbazone, I+thifensulfuron-methyl, I+thiobencarb, I+topramezone, I+tralkoxydim, I+tri-allate, I+triasulfuron, I+triaziflam, I+tribenuron, I+tribenuron-methyl, I+triclopyr, I+trietazine, I+trifloxysulfuron, I+trifloxysulfuron-sodium, I+trifluralin, I+triflusulfuron, I+triflusulfuron-methyl, I+trihydroxytriazine, I+trinexapac-ethyl, I+tritosulfuron, I+[3-[2-chloro-4-fluoro-5-(1-methyl-6-trifluoromethyl-2,4-dioxo-1,2,3,4-tetrahydropyrimidin-3-yl)phenoxy]-2-pyridyloxy]acetic acid ethyl ester (CAS RN 353292-31-6). The compounds of formula (I) and/or compositions of the present invention may also be combined with herbicidal compounds disclosed in WO06/024820 and/or WO07/096576.

The mixing partners of the compound of Formula (I) may also be in the form of esters or salts, as mentioned e.g. in The Pesticide Manual, Sixteenth Edition, British Crop Protection Council, 2012.

The compound of Formula (I) can also be used in mixtures with other agrochemicals such as fungicides, nematicides or insecticides, examples of which are given in The Pesticide Manual (supra).

The mixing ratio of the compound of Formula (I) to the mixing partner is preferably from 1:100 to 1000:1.

The mixtures can advantageously be used in the above-mentioned formulations (in which case "active ingredient" relates to the respective mixture of compound of Formula I with the mixing partner).

The compounds of Formula (I) as described herein can also be used in combination with one or more safeners. Likewise, mixtures of a compound of Formula (I) as described herein with one or more further herbicides can also be used in combination with one or more safeners. The safeners can be AD 67 (MON 4660), benoxacor, cloquintocet-mexyl, cyprosulfamide (CAS RN 221667-31-8), dichlormid, fenchlorazole-ethyl, fenclorim, fluxofenim, furilazole and the corresponding R isomer, isoxadifen-ethyl, mefenpyr-diethyl, oxabetrinil, N-isopropyl-4-(2-methoxybenzoylsulfamoyl)-benzamide (CAS RN 221668-34-4). Other possibilities include safener compounds disclosed in, for example, EP0365484 e.g N-(2-methoxybenzoyl)-4-[methylaminocarbonyl)amino]benzenesulfonamide. Particularly preferred are mixtures of a compound of Formula I with cyprosulfamide, isoxadifen-ethyl, cloquintocet-mexyl and/or N-(2-methoxybenzoyl)-4-[methyl-aminocarbonyl) amino]benzenesulfonamide.

The safeners of the compound of Formula (I) may also be in the form of esters or salts, as mentioned e.g. in The Pesticide Manual (supra). The reference to cloquintocet-mexyl also applies to a lithium, sodium, potassium, calcium, magnesium, aluminium, iron, ammonium, quaternary ammonium, sulfonium or phosphonium salt thereof as disclosed in WO 02/34048, and the reference to fenchlorazole-ethyl also applies to fenchlorazole, etc.

Preferably the mixing ratio of compound of Formula (I) to safener is from 100:1 to 1:10, especially from 20:1 to 1:1.

The mixtures can advantageously be used in the above-mentioned formulations (in which case "active ingredient" relates to the respective mixture of compound of Formula (I) with the safener).

As described above, compounds of formula (I) and/or compositions comprising such compounds may be used in methods of controlling unwanted plant growth, and in particular in controlling unwanted plant growth in crops of useful plants. Thus, the present invention further provides a method of selectively controlling weeds at a locus comprising crop plants and weeds, wherein the method comprises application to the locus, of a weed-controlling amount of a compound of formula (I), or a composition as described herein. 'Controlling' means killing, reducing or retarding growth or preventing or reducing germination. Generally the plants to be controlled are unwanted plants (weeds). 'Locus' means the area in which the plants are growing or will grow.

The rates of application of compounds of Formula (I) may vary within wide limits and depend on the nature of the soil, the method of application (pre- or post-emergence; seed dressing; application to the seed furrow; no tillage application etc.), the crop plant, the weed(s) to be controlled, the prevailing climatic conditions, and other factors governed by the method of application, the time of application and the target crop. The compounds of Formula I according to the invention are generally applied at a rate of from 10 to 2000 g/ha, especially from 50 to 1000 g/ha.

The application is generally made by spraying the composition, typically by tractor mounted sprayer for large areas, but other methods such as dusting (for powders), drip or drench can also be used.

Useful plants in which the composition according to the invention can be used include crops such as cereals, for example barley and wheat, cotton, oilseed rape, sunflower, maize, rice, soybeans, sugar beet, sugar cane and turf.

Crop plants can also include trees, such as fruit trees, palm trees, coconut trees or other nuts. Also included are vines such as grapes, fruit bushes, fruit plants and vegetables.

Crops are to be understood as also including those crops which have been rendered tolerant to herbicides or classes of herbicides (e.g. ALS-, GS-, EPSPS-, PPO-, ACCase- and HPPD-inhibitors) by conventional methods of breeding or by genetic engineering. An example of a crop that has been rendered tolerant to imidazolinones, e.g. imazamox, by conventional methods of breeding is Clearfield® summer rape (canola). Examples of crops that have been rendered tolerant to herbicides by genetic engineering methods include e.g. glyphosate- and glufosinate-resistant maize varieties commercially available under the trade names RoundupReady® and LibertyLink®, as well as those where the crop plant has been engineered to over-express homogentisate solanesyltransferase as taught in, for example, WO2010/029311.

Crops are also to be understood as being those which have been rendered resistant to harmful insects by genetic engineering methods, for example Bt maize (resistant to European corn borer), Bt cotton (resistant to cotton boll weevil) and also Bt potatoes (resistant to Colorado beetle). Examples of Bt maize are the Bt 176 maize hybrids of NK® (Syngenta Seeds). The Bt toxin is a protein that is formed naturally by *Bacillus thuringiensis* soil bacteria. Examples of toxins, or transgenic plants able to synthesise such toxins, are described in EP-A-451 878, EP-A-374 753, WO 93/07278, WO 95/34656, WO 03/052073 and EP-A-427 529. Examples of transgenic plants comprising one or more genes that code for an insecticidal resistance and express one or more toxins are KnockOut® (maize), Yield Gard® (maize), NuCOTIN33B® (cotton), Bollgard@ (cotton), NewLeaf® (potatoes), NatureGard® and Protexcta®. Plant crops or seed material thereof can be both resistant to herbicides and, at the same time, resistant to insect feeding ("stacked" transgenic events). For example, seed can have the ability to express an insecticidal Cry3 protein while at the same time being tolerant to glyphosate.

Crops are also to be understood to include those which are obtained by conventional methods of breeding or genetic engineering and contain so-called output traits (e.g. improved storage stability, higher nutritional value and improved flavour).

Other useful plants include turf grass for example in golf-courses, lawns, parks and roadsides, or grown commercially for sod, and ornamental plants such as flowers or bushes.

The compositions can be used to control unwanted plants (collectively, 'weeds'). The weeds to be controlled include both monocotyledonous (e.g. grassy) species, for example: *Agrostis, Alopecurus, Avena, Brachiaria, Bromus, Cenchrus, Cyperus, Digitaria, Echinochloa, Eleusine, Lolium, Monochoria, Rottboellia, Sagittaria, Scirpus, Setaria* and *Sorghum*; and dicotyledonous species, for example: *Abutilon, Amaranthus, Ambrosia, Chenopodium, Chrysanthemum, Conyza, Galium, Ipomoea, Kochia, Nasturtium, Polygonum, Sida, Sinapis, Solanum, Stellaria, Veronica, Viola* and *Xanthium*. Weeds can also include plants which may be considered crop plants but which are growing outside a crop area ('escapes'), or which grow from seed left over from a previous planting of a different crop ('volunteers'). Such volunteers or escapes may be tolerant to certain other herbicides.

Preferably the weeds to be controlled and/or growth-inhibited, include monocotyledonous weeds, more preferably grassy monocotyledonous weeds, in particular those from the following genus: *Agrostis, Alopecurus, Apera, Avena, Brachiaria, Bromus, Cenchrus, Cyperus* (a genus of sedges), *Digitaria, Echinochloa, Eleusine, Eriochloa, Fimbristylis* (a genus of sedges), *Juncus* (a genus of rushes), *Leptochloa, Lolium, Monochoria, Ottochloa, Panicum, Pennisetum, Phalaris, Poa, Rottboellia, Sagittaria, Scirpus* (a genus of sedges), *Setaria* and/or *Sorghum*, and/or volunteer corn (volunteer maize) weeds; in particular: *Alopecurus myosuroides* (ALOMY, English name "blackgrass"), *Apera spica-venti, Avena fatua* (AVEFA, English name "wild oats"), *Avena ludoviciana, Avena sterilis, Avena sativa* (English name "oats" (volunteer)), *Brachiaria decumbens, Brachiaria plantaginea, Brachiaria platyphylla* (BRAPP), *Bromus tectorum, Digitaria horizontalis, Digitaria insularis, Digitaria sanguinalis* (DIGSA), *Echinochloa crus-galli* (English name "common barnyard grass", ECHCG), *Echinochloa oryzoides, Echinochloa colona* or *colonum, Eleusine indica, Eriochloa villosa* (English name "woolly cupgrass"), *Leptochloa chinensis, Leptochloa panicoides, Lolium perenne* (LOLPE, English name "perennial ryegrass"), *Lolium multiflorum* (LOLMU, English name "Italian ryegrass"), *Lolium persicum* (English name "Persian darnel"), *Lolium rigidum, Panicum dichotomiflorum* (PANDI), *Panicum miliaceum* (English name "wild proso millet"), *Phalaris minor, Phalaris paradoxa, Poa annua* (POAAN, English name "annual bluegrass"), *Scirpus maritimus, Scirpus juncoides, Setaria viridis* (SETVI, English name "green foxtail"), *Setaria faberi* (SETFA, English name "giant foxtail"), *Setaria glauca, Setaria lutescens* (English name "yellow foxtail"), *Sorghum bicolor*, and/or *Sorghum halepense* (English name "Johnson grass"), and/or *Sorghum vulgare*; and/or volunteer corn (volunteer maize) weeds.

In one embodiment, grassy monocotyledonous weeds to be controlled comprise weeds from the genus: *Agrostis, Alopecurus, Apera, Avena, Brachiaria, Bromus, Cenchrus, Digitaria, Echinochloa, Eleusine, Eriochloa, Leptochloa, Lolium, Ottochloa, Panicum, Pennisetum, Phalaris, Poa, Rottboellia, Setaria* and/or *Sorghum*, and/or volunteer corn (volunteer maize) weeds; in particular: weeds from the genus *Agrostis, Alopecurus, Apera, Avena, Brachiaria, Bromus, Cenchrus, Digitaria, Echinochloa, Eleusine, Eriochloa, Leptochloa, Lolium, Panicum, Phalaris, Poa, Rottboellia, Setaria*, and/or *Sorghum*, and/or volunteer corn (volunteer maize) weeds.

In a further embodiment, the grassy monocotyledonous weeds are "warm-season" (warm climate) grassy weeds; in which case they preferably comprise (e.g. are): weeds from the genus *Brachiaria, Cenchrus, Digitaria, Echinochloa, Eleusine, Eriochloa, Leptochloa, Ottochloa, Panicum, Pennisetum, Phalaris, Rottboellia, Setaria* and/or *Sorghum*, and/or volunteer corn (volunteer maize) weeds. More preferably, the grassy monocotyledonous weeds, e.g. to be controlled and/or growth-inhibited, are "warm-season" (warm climate) grassy weeds comprising (e.g. being): weeds from the genus *Brachiaria, Cenchrus, Digitaria, Echinochloa, Eleusine, Eriochloa, Panicum, Setaria* and/or *Sorghum*, and/or volunteer corn (volunteer maize) weeds.

In another particular embodiment the grassy monocotyledonous weeds, are "cool-season" (cool climate) grassy weeds; in which case they typically comprise weeds from the genus *Agrostis, Alopecurus, Apera, Avena, Bromus, Lolium* and/or *Poa*.

Various aspects and embodiments of the present invention will now be illustrated in more detail by way of example. It will be appreciated that modification of detail may be made without departing from the scope of the invention.

PREPARATION EXAMPLES

[Pd(IPr*)(cin)Cl] refers to chlorophenylallyl[1,3-bis[2,6-bis(diphenylmethyl)-4-methylphenyl-imidazol-2-ylidene]palladium(II) [1380314-24-8]—see *Chem. Eur. J.* 2012, 18, 4517

'BuBrettPhos Pd G3 refers to methanesulfonato(2-(di-t-butylphosphino)-3,6-dimethoxy-2',4',6'-tri-i-propyl-1,1'-biphenyl)(2'-amino-1,1'-biphenyl-2-yl)palladium(II), dichloromethane adduct [1536473-72-9]

Example P1: Synthesis of 2-(5-fluoro-3-pyridyl)-N,4-dimethyl-pyrimidin-5-amine (Compound D1)

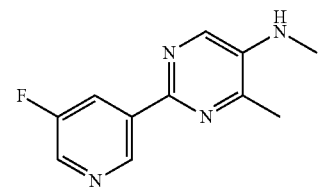 [SMILES: CNc1cnc(-c2cncc(F)c2)nc1C]

Step 1: Synthesis of tert-butyl N-(2-chloro-4-methyl-pyrimidin-5-yl)carbamate

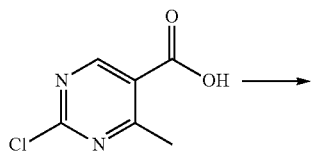

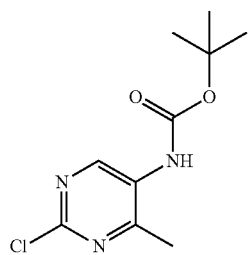

To a stirred solution of 2-chloro-4-methyl-pyrimidine-5-carboxylic acid (500 mg, 2.90 mmol) and triethylamine (0.53 mL, 3.77 mmol) in tert-butanol (25 mL) was added diphenylphosphoryl azide (0.81 mL, 3.77 mmol). The reaction mixture heated to 90° C. for 4 hours and then allowed to cool to RT overnight. The reaction mixture was diluted with water (100 mL) and extracted with EtOAc (3×25 mL). The combined organic extracts were washed with brine (20 mL), dried over MgSO$_4$ and evaporated to dryness under reduced pressure to give a yellow oil. The crude product was purified by flash chromatography on silica gel using an EtOAc/isohexane gradient as eluent to give the desired product (527 mg, 75%) as a white solid.

$^1$H NMR (400 MHz, CDCl$_3$) δ=9.03 (br s, 1H), 6.42 (br s, 1H), 2.50 (s, 3H), 1.53 (s, 9H).

Step 2: Synthesis of tert-butyl N-[2-(5-fluoro-3-pyridyl)-4-methyl-pyrimidin-5-yl]carbamate

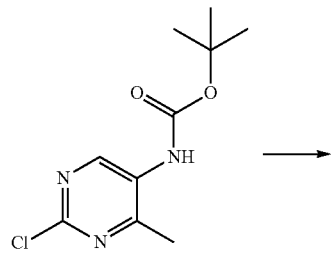

A mixture of tert-butyl N-(2-chloro-4-methyl-pyrimidin-5-yl)carbamate (212 mg, 0.87 mmol), 5-fluoropyridine-3-boronic acid (160 mg, 1.09 mmol), potassium carbonate (265 mg, 1.91 mmol) and [Pd(IPr*)(cin)Cl] (50 mg, 0.043 mmol) in EtOH (6.40 mL) was heated at 80° C. under an N2 atmosphere for 1 hour. The mixture was filtered through celite, washed through with EtOH and evaporated to dryness under reduced pressure to give an orange-brown gum. The crude product was purified by flash chromatography on silica gel using an EtOAc/isohexane gradient as eluent to give the desired product (170 mg, 64%) as a yellow solid.

$^1$H NMR (400 MHz, CDCl$_3$) δ=9.42 (s, 1H), 9.20 (br s, 1H), 8.52 (d, 1H), 8.38 (dd, 1H), 6.55 (br s, 1H), 2.57 (s, 3H), 1.55 (s, 9H).

Step 3: Synthesis of tert-butyl N-[2-(5-fluoro-3-pyridyl)-4-methyl-pyrimidin-5-yl]-N-methyl-carbamate

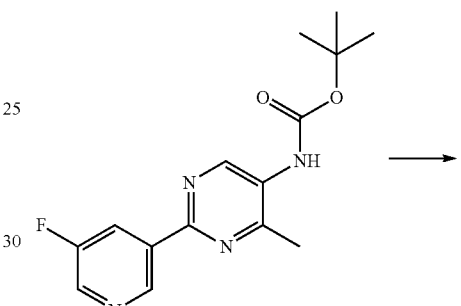

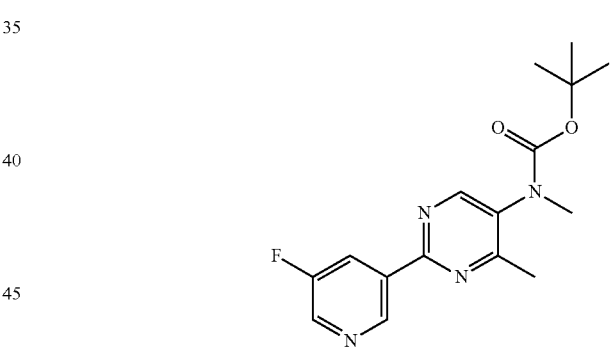

To a stirred solution of tert-butyl N-[2-(5-fluoro-3-pyridyl)-4-methyl-pyrimidin-5-yl]carbamate (246 mg, 0.81 mmol) in tetrahydrofuran (5 mL) at RT under an N$_2$ atmosphere was added in a single portion NaH (60% dispersion in mineral oil) (34 mg, 0.85 mmol). The reaction was then stirred at RT for 20 minutes and then iodomethane (0.051 mL, 0.81 mmol) was added and the reaction was stirred for 1 hour. The reaction was quenched with H$_2$O (5 mL) and HCl (to acidic pH) was added and the reaction extracted with EtOAc (3×10 mL). The combined organic extracts were washed with brine (10 mL), dried over MgSO$_4$ and evaporated to dryness under reduced pressure. The crude product was purified by flash chromatography on silica gel using an EtOAc/isohexane gradient as eluent to give the desired product (257 mg, 81%) as a yellow solid.

$^1$H NMR (400 MHz, CDCl$_3$) δ=9.47 (br s, 1H), 8.63-8.48 (m, 2H), 8.42 (br d, 1H), 3.23 (s, 3H), 2.53 (s, 3H), 1.60-1.28 (br m, 9H).

Step 4: Synthesis of 2-(5-fluoro-3-pyridyl)-N,4-dimethyl-pyrimidin-5-amine (Compound D1)

Step 1: Synthesis of 2-(5-fluoro-3-pyridyl)-4-methyl-pyrimidin-5-amine (Compound D2)

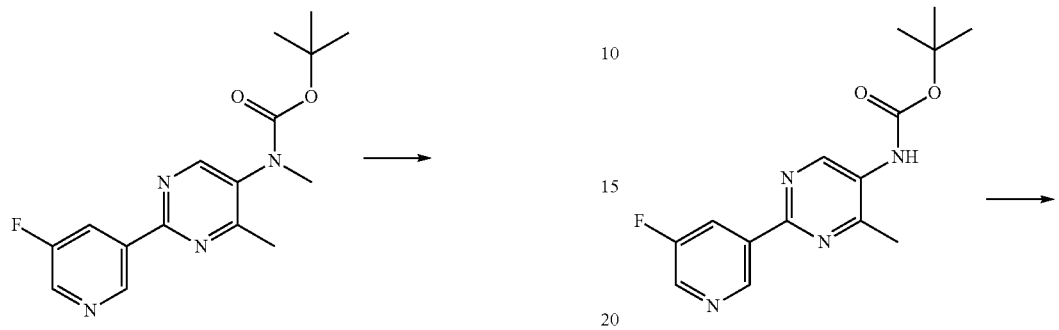

To a stirred solution of tert-butyl N-[2-(5-fluoro-3-pyridyl)-4-methyl-pyrimidin-5-yl]-N-methyl-carbamate (113 mg, 0.35 mmol) in DCM (5 mL) was added trifluoroacetic acid (0.14 mL, 1.77 mmol) and the reaction stirred at RT for 4 days. Further trifluoroacetic acid (0.14 mL) and DCM (2 mL) were added and the reaction was heated at reflux for 3 hours. The reaction was allowed to cool to RT overnight and then quenched with saturated aqueous NaHCO$_3$ solution until effervescence ceased and the reaction was then extracted with DCM 3×10 mL). The combined organic extracts were dried and evaporated to dryness under reduced pressure. The crude product was purified by flash chromatography on silica gel using an EtOAc/isohexane gradient as eluent to give the desired product (59 mg, 76%) as a beige solid.

$^1$H NMR (400 MHz, CD$_3$OD) δ 9.23 (s, 1H), 8.42 (d, 1H), 8.37-8.29 (m, 1H), 8.02 (s, 1H), 2.93 (s, 3H), 2.44 (s, 3H).

To a stirred solution of tert-butyl N-[2-(5-fluoro-3-pyridyl)-4-methyl-pyrimidin-5-yl]carbamate (156 mg, 0.51 mmol) in DCM (5 mL) was added trifluoroacetic acid (0.24 mL, 3.08 mmol) and the reaction was stirred at RT overnight and then heated to reflux for 7 hours. Further TFA (0.24 mL) was added and the reaction was stood at RT for 72 hours. The reaction was quenched with saturated aqueous NaHCO$_3$ solution until effervescence ceased and the reaction was then extracted with DCM (3×10 mL). The combined organic extracts were dried and evaporated to dryness under reduced pressure. The crude product was purified by flash chromatography on silica gel using an EtOAc/isohexane gradient as eluent followed by mass-directed reverse phase HPLC to give the desired product (19 mg, 15%) as a yellow solid.

$^1$H NMR (400 MHz, CDCl$_3$) δ=9.41 (s, 1H), 8.60-8.48 (m, 2H), 8.16 (s, 1H), 6.30 (br s, 2H), 2.48 (s, 3H).

Example P2: Synthesis of 2-(5-fluoro-3-pyridyl)-4-methyl-pyrimidin-5-amine (Compound D2)

Example P3: Synthesis of 4-methyl-2-pyrimidin-5-yl-pyrimidin-5-amine (Compound D3)

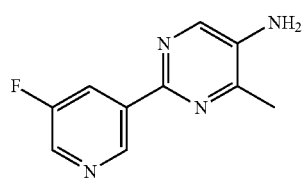

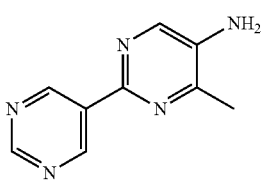

Step 1: Synthesis of tert-butyl N-(4-methyl-2-pyrimidin-5-yl-pyrimidin-5-yl)carbamate

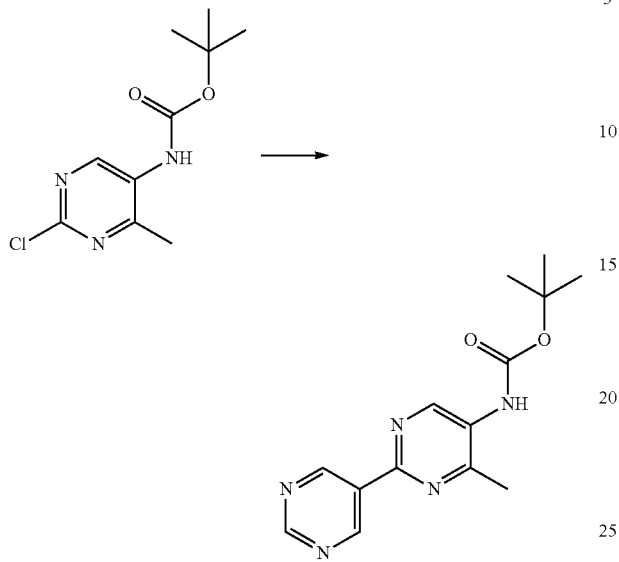

A mixture of tert-butyl N-(2-chloro-4-methyl-pyrimidin-5-yl)carbamate (1.93 g, 7.92 mmol), pyrimidin-5-ylboronic acid (1.47 g, 11.9 mmol), K₂CO₃ (2.41 g, 17.4 mmol) and [Pd(IPr*)(cin)Cl] (0.464 g, 0.40 mmol) in EtOH (40 mL) was heated at 80° C. for 1.5 hours. The reaction was cooled to RT, filtered through celite, washed through with EtOH and evaporated to dryness under reduced pressure to give an orange-brown gum. The crude product was purified by flash chromatography on silica gel using an EtOAc/isohexane gradient as eluent to give the desired product (1.69 g, 74%) as a pale yellow solid.

$^1$H NMR (400 MHz, CDCl₃) δ=9.65 (s, 2H), 9.27 (s, 1H), 9.25 (br s, 1H), 6.38 (br s, 1H), 2.58 (s, 3H), 1.56 (s, 9H).

Step 2: Synthesis of 4-methyl-2-pyrimidin-5-yl-pyrimidin-5-amine (Compound D3)

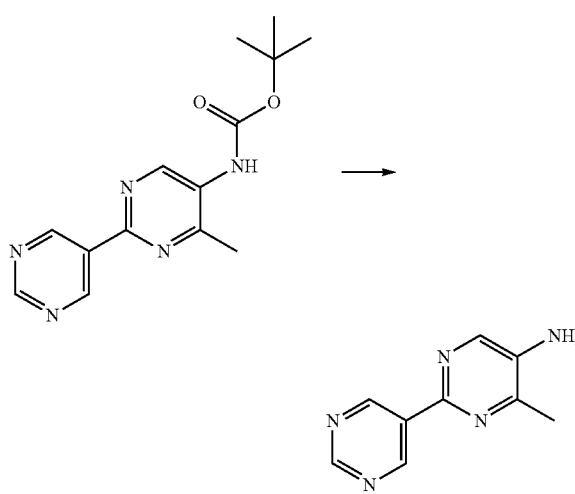

To a stirred solution of tert-butyl N-(4-methyl-2-pyrimidin-5-yl-pyrimidin-5-yl)carbamate (400 mg, 1.39 mmol) in DCM (5 mL) was added trifluoroacetic acid (0.53 mL, 6.96 mmol) and the reaction was stirred at RT overnight. Further trifluoroacetic acid (0.53 mL) was added and the reaction was heated at reflux for 4 hours. The reaction was cooled to RT and evaporated to dryness. The crude product was purified by flash chromatography on silica gel using an EtOAc/isohexane gradient as eluent to give the desired product (233 mg, 89%) as a pale yellow solid.

$^1$H NMR (400 MHz, CDCl₃) δ=9.59 (s, 2H), 9.22 (s, 1H), 8.17 (s, 1H), 3.85 (br s, 2H), 2.49 (s, 3H).

Example P4: Synthesis of 2-(5-fluoro-3-pyridyl)-4-(trifluoromethyl)pyrimidin-5-amine (Compound D5)

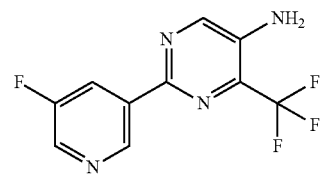 [SMILES: Nc1cnc(-c2cncc(F)c2)nc1C(F)(F)F]

Route 1, step 1: Synthesis of tert-butyl N-[2-chloro-4-(trifluoromethyl)pyrimidin-5-yl]carbamate

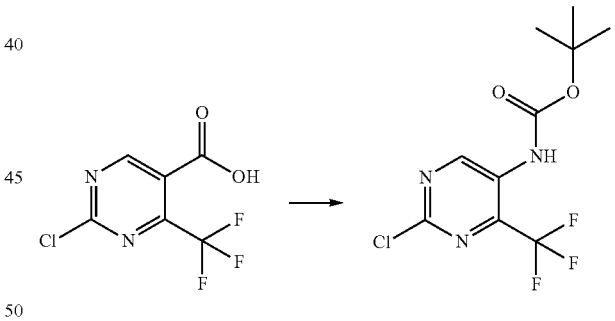

To a stirred solution of 2-chloro-4-(trifluoromethyl)pyrimidine-5-carboxylic acid (0.95 g, 4.19 mmol) and triethylamine (0.76 mL, 5.45 mmol) in tert-butanol (7.5 mL) and toluene (5 mL) at reflux was added dropwise a solution of diphenylphosphoryl azide (1.17 mL, 5.45 mmol) in toluene (2.5 mL). The reaction was heated at reflux for 2 hours and then allowed to cool to RT. The reaction mixture was diluted with EtOAc (100 mL), washed with brine (100 mL). The aqueous phase was extracted with further EtOAc (2×100 mL), the combined organic extracts were dried over MgSO₄ and evaporated to dryness under reduced pressure. The crude product was purified by flash chromatography on silica gel using an EtOAC/isohexane gradient as eluent to give the desired product (0.46 g, 37%) as a colourless solid.

$^1$H NMR (400 MHz, CDCl₃) δ 9.68 (s, 1H), 6.80 (br s, 1H), 1.55 (s, 9H).

Route 1, step 2: Synthesis of tert-butyl N-[2-(5-fluoro-3-pyridyl)-4-(trifluoromethyl)pyrimidin-5-yl]carbamate

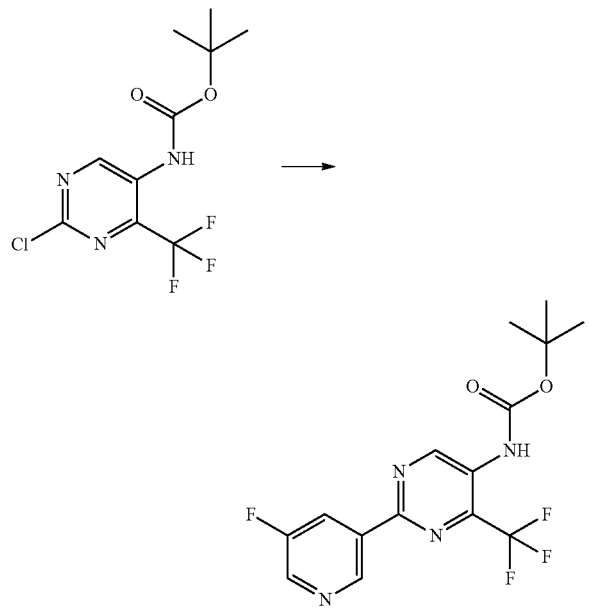

A mixture of tert-butyl N-[2-chloro-4-(trifluoromethyl)pyrimidin-5-yl]carbamate (0.20 g, 0.672 mmol) and (5-fluoro-3-pyridyl)boronic acid (0.133 g, 0.941 mmol) in EtOH (0.54 mL), toluene (2 mL) and water (0.92 mL) was sparged with $N_2$ for 30 min at RT. $K_2CO_3$ (0.186 g, 1.34 mmol) and Pd(PPh$_3$)$_4$ (0.039 g, 0.0336 mmol) were then added and the yellow solution heated to 85° C. under an N2 atmosphere for 8 hours and cooled to RT overnight. The mixture was diluted with EtOAc (30 mL) and washed with brine (30 mL). The aqueous layer was then extracted with further EtOAc (2×30 mL) and the combined organic extracts were dried over MgSO$_4$ and evaporated to dryness under reduced pressure. The crude product was purified by flash chromatography on silica gel using an EtOAc/isohexane gradient as eluent to give the desired product (0.224 g, 93%) as a colourless solid.

$^1$H NMR (400 MHz, CDCl$_3$) δ 9.81 (s, 1H), 9.45 (s, 1H), 8.58 (d, 1H), 8.39 (d, 1H), 6.97 (br s, 1H), 1.58 (m, 9H).

Route 2, Step 1: Synthesis of ethyl (2E/Z)-2-(ethoxymethylene)-4,4,4-trifluoro-3-oxo-butanoate

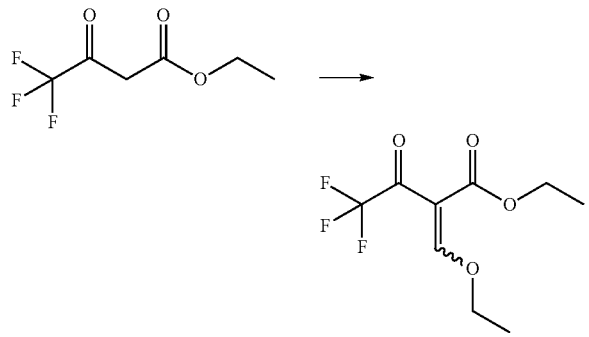

A mixture of acetic anhydride (30.8 mL, 325.9 mmol), triethyl orthoformate (36.1 mL, 217.3 mmol) and ethyl 4,4,4-trifluoro-3-oxo-butanoate (15.89 mL, 108.6 mmol) was heated at reflux for 6 hours and then allowed to cool to RT. The excess reagents were removed by distillation under reduced pressure to leave the desired product as a mixture of E/Z isomers (23.2 g, 89%) as an orange oil.

$^1$H NMR (400 MHz, CDCl$_3$) δ 7.83 and 7.72 (2×s, 1H), 4.40-4.20 (m, 4H), 1.49-1.22 (m, 3H).

Route 2, Step 2: Synthesis of (5-fluoropyridine-3-carboximidoyl)ammonium chloride

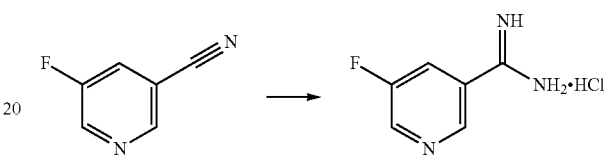

To a stirred solution of 5-fluoropyridine-3-carbonitrile (2.0 g, 16.38 mmol) in methanol (20 mL) at RT was added NaOMe (88 mg, 1.64 mmol) and the reaction stirred at RT overnight. Ammonium chloride (1.40 g, 26.21 mmol) was added in a single portion and the reaction mixture stirred overnight at RT. The reaction mixture was filtered and the filtrate concentrated to dryness under reduced pressure. The residue was suspended in EtOH (50 mL) and then heated at reflux. The undissolved solid was filtered off and the filtrate concentrated to ⅓ of its volume and then left to stand at RT. The resultant crystals were filtered off, washed with EtOH and air-dried to give the desired product (2.11 g, 73%) as white crystals.

$^1$H NMR (400 MHz, d6-DMSO) δ 8.93 (d, 1H), 8.88 (s, 1H), 8.29-8.23 (m, 1H).

Route 2, Step 3: Synthesis of ethyl 2-(5-fluoro-3-pyridyl)-4-(trifluoromethyl)pyrimidine-5-carboxylate

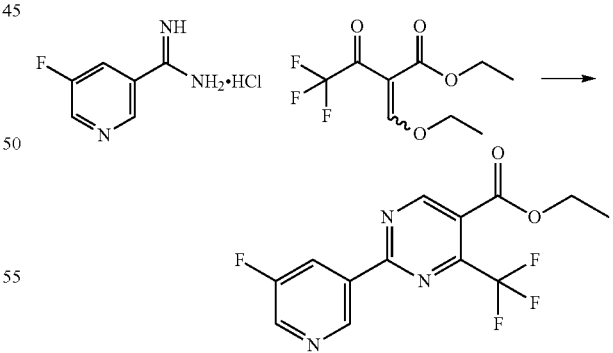

To a stirred solution of (5-fluoropyridine-3-carboximidoyl)ammonium chloride (2.0 g, 11.4 mmol) and ethyl (2E/Z)-2-(ethoxymethylene)-4,4,4-trifluoro-3-oxo-butanoate (2.74 g, 11.4 mmol) in EtOH (40 mL) was added NaOEt (1.16 g, 17.1 mmol). The reaction was heated at reflux for 2 hrs and then further NaOEt (155 mg, 0.2 equiv) was added, the reaction mixture heated at reflux for a further 1 hr and then allowed to cool to RT overnight.

The reaction mixture was evaporated to dryness under reduced pressure and the residue partitioned between water (25 mL) and extracted with EtOAc (3×20 mL). The combined organic extracts were washed with brine (20 mL), dried over MgSO$_4$ and evaporated to dryness under reduced pressure to give an orange oil. The crude product was purified by flash chromatography on silica gel using a gradient of 5-25% ethyl acetate in isohexane as eluent to give the desired product (2.15 g, 60%) as an off-white solid.

$^1$H NMR (400 MHz, CDCl$_3$) δ 9.57 (s, 1H), 9.32 (s, 1H), 8.66 (d, 1H), 8.52-8.47 (m, 1H), 4.49 (q, 2H), 1.44 (t, 3H).

Route 2, Step 4: Synthesis of 2-(5-fluoro-3-pyridyl)-4-(trifluoromethyl)pyrimidine-5-carboxylic Acid

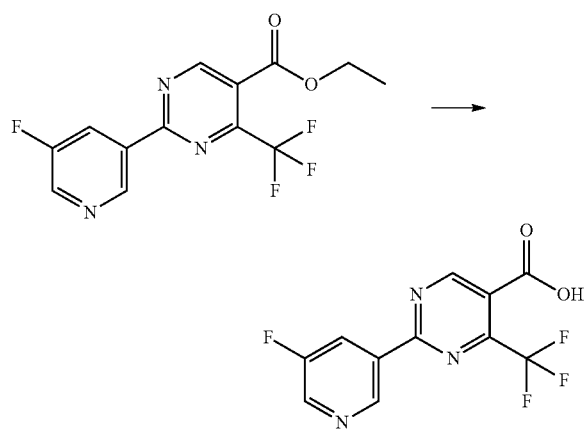

To a stirred solution of ethyl 2-(5-fluoro-3-pyridyl)-4-(trifluoromethyl)pyrimidine-5-carboxylate (2.15 g, 6.82 mmol) in EtOH (60 mL) and water (20 mL) was added LiOH (0.49 g, 20.5 mmol). The reaction was stirred at RT for 3 hours. The EtOH was removed under reduced pressure and the resulting residue diluted with water (30 mL), acidified with 2M HCl to pH 5 and extracted with EtOAc (3×25 mL). The combined organic extracts were washed with brine (15 mL), dried over MgSO$_4$ and evaporated to dryness under reduced pressure to give the desired product (1.34 g, 68%) as a white powder.

$^1$H NMR (400 MHz, d6-DMSO) δ 9.50 (s, 1H), 9.41 (s, 1H), 8.88 (s, 1H), 8.52-8.45 (m, 1H).

Route 2, Step 5: Synthesis of tert-butyl N-[2-(5-fluoro-3-pyridyl)-4-(trifluoromethyl)pyrimidin-5-yl]carbamate

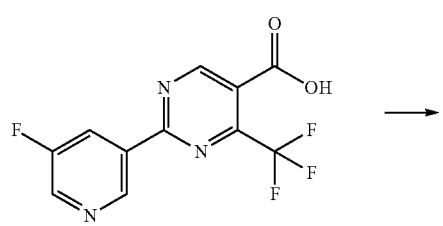

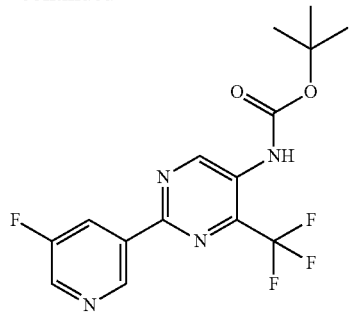

To a stirred solution of 2-(5-fluoro-3-pyridyl)-4-(trifluoromethyl)pyrimidine-5-carboxylic acid (1.30 g, 4.53 mmol) and triethylamine (0.82 mL, 5.89 mmol) in tert-butanol (12 mL) and toluene (6 mL) at reflux was added dropwise over 5 minutes a solution of diphenylphosphoryl azide (1.27 mL, 5.89 mmol) in toluene (6 mL). The reaction was heated at reflux for 3 hours, then allowed to cool to RT, diluted with EtOAc (60 mL) and washed with brine (60 mL). The aqueous layer was extracted with further EtOAc (2×100 mL). The combined organic extracts were dried over MgSO$_4$ and evaporated to dryness under reduced pressure. The crude product was purified by flash chromatography on silica gel using an EtOAc/isohexane gradient as eluent to give the desired product (941 mg, 59%) as a colourless solid.

$^1$H NMR (400 MHz, CDCl$_3$) δ 9.81 (s, 1H), 9.45 (s, 1H), 8.58 (d, 1H), 8.39 (d, 1H), 6.97 (br s, 1H), 1.58 (m, 9H)

Route 1, step 3 and route 2, step 6: Synthesis of 2-(5-fluoro-3-pyridyl)-4-(trifluoromethyl)pyrimidin-5-amine (Compound D5)

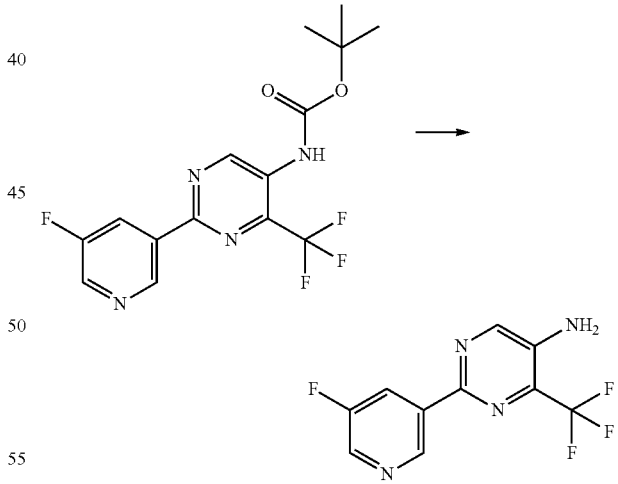

To a stirred solution of tert-butyl N-[2-(5-fluoro-3-pyridyl)-4-(trifluoromethyl)pyrimidin-5-yl]carbamate (250 mg, 0.70 mmol) in DCM (5 mL) was added trifluoroacetic acid (0.53 mL, 7.0 mmol) and the reaction was heated at reflux for 6 hours and then allowed to cool to RT overnight. Saturated aqueous NaHCO$_3$ solution was added until effervescence ceased and then the reaction was extracted into with DCM (3×10 mL). The combined organic extracts were dried and evaporated to dryness under reduced pressure. The crude product was purified by flash chromatography on silica gel using an EtOAc/isohexane gradient as eluent to give the desired product (148 mg, 82%) as a white solid. $^1$H NMR (400 MHz, CDCl$_3$) δ=9.37 (s, 1H), 8.53-8.46 (m, 2H), 8.30 (d, 1H), 4.44 (br s, 2H).

Example P5: Synthesis of 5-[5-amino-4-(trifluoromethyl)pyrimidin-2-yl]pyridine-3-carbonitrile (Compound D10)

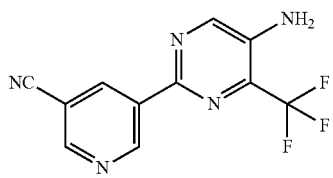 [SMILES: N#Cc1cncc(-c2ncc(N)c(C(F)(F)F)n2)c1]

Step 1: Synthesis of 5-chloro-2-methylsulfanyl-4-(trifluoromethyl)pyrimidine

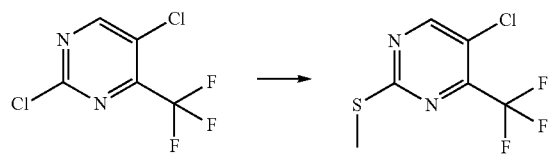

To a stirred suspension of NaSMe (0.17 g, 2.42 mmol) in MeOH (5 mL) at RT was added 2,5-dichloro-4-(trifluoromethyl)pyrimidine (0.50 g, 2.30 mmol). The reaction was heated at reflux for 2¼ hours, allowed to cool to RT and then evaporated to dryness under reduced pressure to give a pale yellow paste. The crude material was dissolved in EtOAc (20 mL) and washed with H$_2$O (3×20 mL). The organic phase was then dried over MgSO$_4$ and evaporated to dryness under reduced pressure to give a pale yellow oil. The crude product was purified by flash chromatography on silica gel using an EtOAc/isohexane gradient as eluent to give the desired product (0.419 g, 80%) as a colourless oil. $^1$H NMR (400 MHz, CDCl3) δ 8.66 (s, 1H), 2.60 (s, 3H).

Step 2: Synthesis of 5-[5-chloro-4-(trifluoromethyl)pyrimidin-2-yl]pyridine-3-carbonitrile

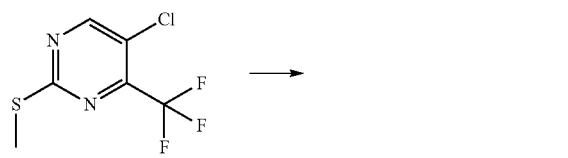

A microwave vial was charged with 5-chloro-2-methylsulfanyl-4-(trifluoromethy)pyrimidine (0.175 g, 0.77 mmol), (5-cyano-3-pyridyl)boronic acid (0.170 g, 1.15 mmol), Pd$_2$dba$_3$ (0.028 g, 0.031 mmol), tris(2-furyl)phosphane (0.028 g, 0.122 mmol), copper(I) 3-methylsalicylate (0.411 g, 1.91 mmol) and THF (4.67 mL), capped and then degassed by evacuating and purging with N$_2$ three times. The reaction was heated at 100° C. for 1 hour under microwave irradiation. The reaction mixture was diluted with Et$_2$O (25 mL) and washed with 1:2 water:conc. ammonia solution (10 mL). The aqueous phase was extracted with further Et$_2$O (2×25 mL) and the combined organic extracts were washed with 1:2 water:conc. ammonia solution (10 mL), brine (10 mL), dried over MgSO$_4$ and evaporated to dryness under reduced pressure to give a brown gum. The crude product was purified by flash chromatography on silica gel using an EtOAc/isohexane gradient as eluent to give the desired product (0.096 g, 44%) as an off-white solid.

1H NMR (400 MHz, CDCl$_3$): δ 9.84 (s, 1H), 9.08-8.98 (m, 3H)

Step 3: Synthesis of 5-[5-amino-4-(trifluoromethyl)pyrimidin-2-yl]pyridine-3-carbonitrile (Compound D10)

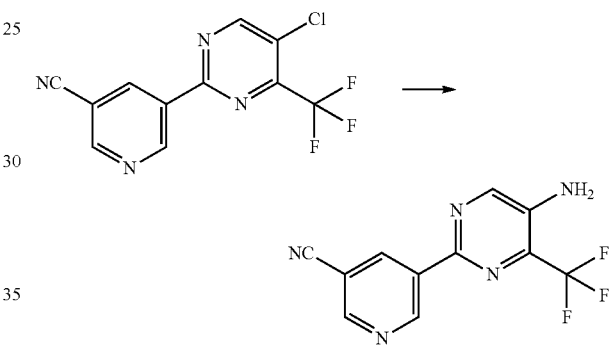

A microwave vial was charged with 5-[5-chloro-4-(trifluoromethyl)pyrimidin-2-yl]pyridine-3-carbonitrile (80 mg, 0.25 mmol), sodium cyanate (37 mg, 0.56 mmol), $^t$BuBrettPhos Pd G3 (10 mg, 0.011 mmol) and anhydrous t-BuOH (1.6 mL), capped and then degassed by evacuating and purging with N$_2$ three times. The reactions was heated at 140° C. for 1 hour under microwave irradiation. The reaction mixture was evaporated to dryness under reduced pressure and the residue purified by flash chromatography on silica gel using an EtOAc/isohexane gradient as eluent to give the desired product (20 mg, 27%) as a beige solid.

$^1$H NMR (400 MHz, CDCl$_3$) δ 9.72 (d, 1H), 8.92-8.89 (m, 1H), 8.89-8.87 (m, 1H), 8.52 (s, 1H), 4.54 (br s, 2H).

Example P6: Synthesis of 2-(5-fluoro-3-pyridyl)-N-propyl-4-(trifluoromethyl)-pyrimidin-5-amine (compound D13) and 2-(5-fluoro-3-pyridyl)-N,N-dipropyl-4-(trifluoromethyl)pyrimidin-5-amine (Compound D14)

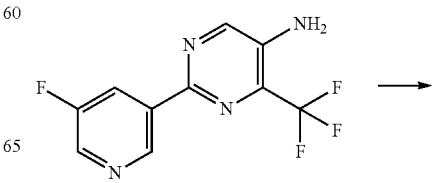

-continued

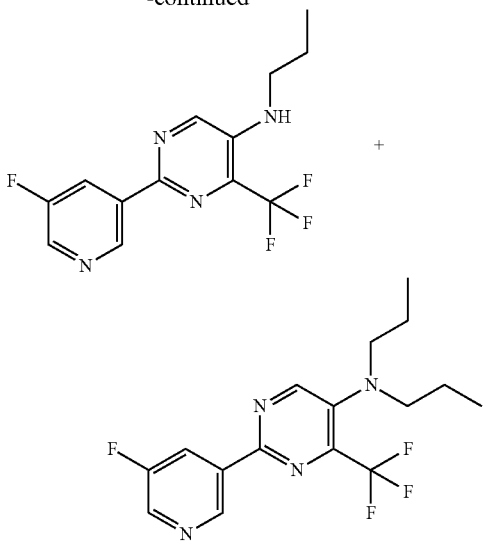

To a stirred solution of 2-(5-fluoro-3-pyridyl)-4-(trifluoromethyl)pyrimidin-5-amine (100 mg, 0.387 mmol) and propionaldehyde (39.5 μL, 0.542 mmol) in ethyl acetate (1.20 mL) was added 2,2,2-trifluoroacetic acid (90.0 μL, 1.16 mmol) followed by careful addition of sodium acetoxyborohydride (160 mg, 0.736 mmol). After 10-15 minutes a homogeneous solution had formed.

The reactions mixture was quenched with 2N NaOH (2 mL) and extracted with EtOAc (2×3 mL). The combined organic extracts were washed with $H_2O$ and brine, dried over $MgSO_4$, filtered and concentrated under reduced pressure to leave a yellow solid. The mixture was purified by flash co,lumn chromatography on silica gel using an EtOAx/isohexane gradient as eluent to give 2-(5-fluoro-3-pyridyl)-N-propyl-4-(trifluoromethyl)pyrimidin-5-amine (D13) (58 mg, 50%) as a white solid and 2-(5-fluoro-3-pyridyl)-N,N-dipropyl-4-(trifluoromethyl)pyrimidin-5-amine (D14) (5 mg, 4%) as a colourless gum.

2-(5-fluoro-3-pyridyl)-N-propyl-4-(trifluoromethyl)pyrimidin-5-amine (D13) $^1$H NMR (400 MHz, CDCl3) δ 9.34 (s, 1H), 8.49 (d, 2H), 8.27 (d, 1H), 4.57 (br s, 1H), 3.31 (q, 2H), 1.65 (m, 2H), 1.08 (t, 3H)

2-(5-fluoro-3-pyridyl)-N,N-dipropyl-4-(trifluoromethyl)pyrimidin-5-amine (D14) $^1$H NMR (400 MHz, $CDCl_3$) δ 9.41 (s, 1H), 8.73 (s, 1H), 8.53 (s, 1H), 8.36 (d, 1H), 3.20 (t, 4H), 1.57 (m, 4H), 0.89 (t, 6H)

Further examples of the invention were made in an analogous manner using the methods described above in Examples P1 to P6, with respect to compounds D1, D2, D3, D5, D10, D13 and D14. Table 2 below, shows the structure of these compounds and the physical characterising data obtained using one or more of methods A to C as outlined below.

TABLE 2

Characterising data for Compounds of formula (I) made by the methods described above.

| Cmpd ID | Structure | $^1$H NMR Data (400MHz, $CDCl_3$ unless stated) |
|---|---|---|
| D1 | 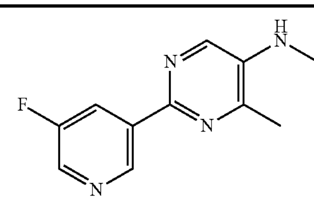 | ($CD_3OD$) 9.23 (s, 1H), 8.42 (d, 1H), 8.37-8.29 (m, 1H), 8.02 (s, 1H), 2.93 (s, 3H), 2.44 (s, 3H) |
| D2 | 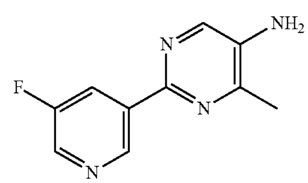 | 9.41 (s, 1H), 8.60-8.48 (m, 2H), 8.16 (s, 1H), 6.30 (br s, 2H), 2.48 (s, 3H) |
| D3 | 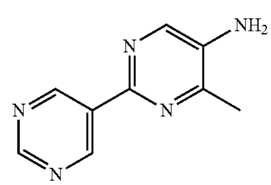 | 9.59 (s, 2H), 9.22 (s, 1H), 8.17 (s, 1H), 3.85 (br s, 2H), 2.49 (s, 3H) |
| D4 | 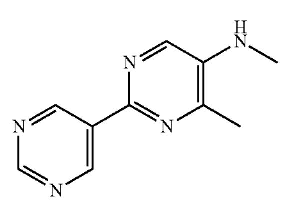 | 9.58 (s, 2H), 9.20 (s, 1H), 8.07 (s, 1H), 3.85 (br s, 1H), 3.01 (s, 3H), 2.46 (s, 3H) |

TABLE 2-continued

Characterising data for Compounds of formula (I) made by the methods described above.

| Cmpd ID | Structure | ¹H NMR Data (400MHz, CDCl₃ unless stated) |
|---|---|---|
| D5 | 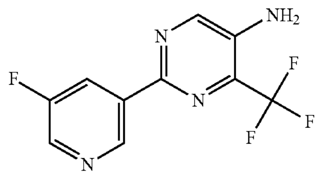 [SMILES: Nc1cnc(-c2cncc(F)c2)nc1C(F)(F)F] | 9.37 (s, 1H), 8.53-8.46 (m, 2H), 8.30 (d, 1H), 4.44 (br s, 2H) |
| D6 | 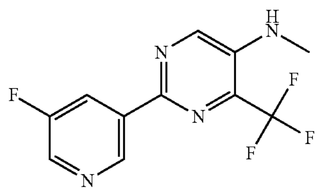 [SMILES: CNc1cnc(-c2cncc(F)c2)nc1C(F)(F)F] | 9.37 (s,1H), 8.45-8.53 (m, 2H), 8.29 (d, 1H), 4.68 (br s, 1H), 3.08 (d, 3H) |
| D7 | 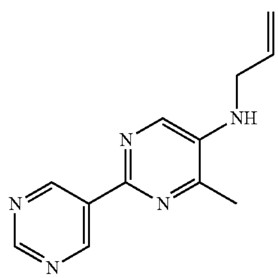 [SMILES: C=CCNc1cnc(-c2cncnc2)nc1C] | (CD₃OD) 9.51 (s, 2H), 9.15 (s, 1H), 8.01 (s, 1H), 5.94 (m, 1H), 5.30-5.19 (m, 2H), 3.95 (m, 2H), 2.96 (s, 3H) |
| D8 | 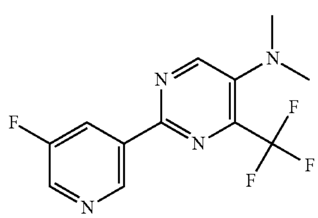 [SMILES: CN(C)c1cnc(-c2cncc(F)c2)nc1C(F)(F)F] | 9.41 (br s, 1H), 8.68 (s, 1H), 8.53 (br s, 1H), 8.35-8.30 (m, 1H), 3.02 (s, 6H). |
| D9 | 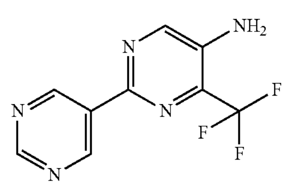 [SMILES: Nc1cnc(-c2cncnc2)nc1C(F)(F)F] | 9.59 (s, 2H), 9.27 (s, 1H), 8.51 (s, 1H), 4.50 (br s, 2H) |
| D10 | 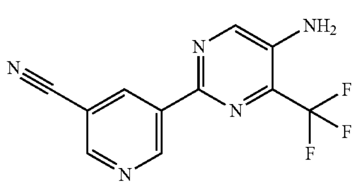 [SMILES: N#Cc1cncc(-c2ncc(N)c(C(F)(F)F)n2)c1] | 9.72 (d, 1H), 8.92-8.89 (m, 1H), 8.89-8.87 (m, 1H), 8.52 (s, 1H), 4.54 (br s, 2H) |
| D11 | 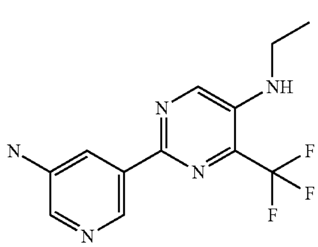 [SMILES: CCNc1cnc(-c2cncc(N)c2)nc1C(F)(F)F] | 9.34 (s, 1H), 8.50 (s, 1H), 8.46 (s, 1H), 8.27 (d, 1H), 4.49 (br s, 1H), 3.52-3.46 (m, 2H), 1.38 (t, 3H) |

TABLE 2-continued

Characterising data for Compounds of formula (I) made by the methods described above.

| Cmpd ID | Structure | ¹H NMR Data (400MHz, CDCl₃ unless stated) |
|---|---|---|
| D12 | 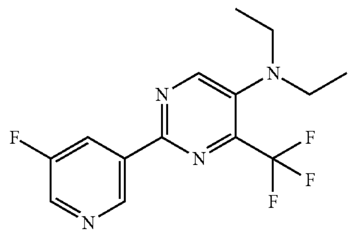 [SMILES: CCN(CC)c1cnc(-c2cncc(F)c2)nc1C(F)(F)F] | 9.44 (s, 1H), 8.75 (s, 1H), 8.56 (s, 1H), 8.38 (d, 1H), 3.27 (q, 4H), 1.14 (t, 6H) |
| D13 | 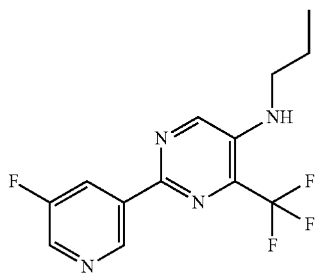 [SMILES: CCCNc1cnc(-c2cncc(F)c2)nc1C(F)(F)F] | 9.34 (s, 1H), 8.49 (d, 2H), 8.27 (d, 1H), 4.57 (b rs, 1H), 3.31 (q, 2H), 1.65 (m, 2H), 1.08 (t, 3H) |
| D14 | 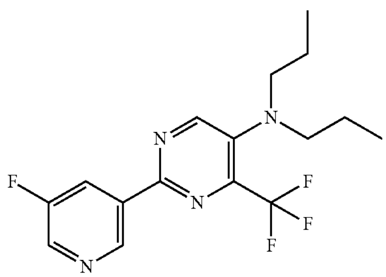 [SMILES: CCCN(CCC)c1cnc(-c2cncc(F)c2)nc1C(F)(F)F] | 9.41 (s, 1H), 8.73 (s, 1H), 8.53 (s, 1H), 8.36 (d, 1H), 3.20 (t, 4H), 1.57 (m, 4H), 0.89 (t, 6H) |
| D15 | 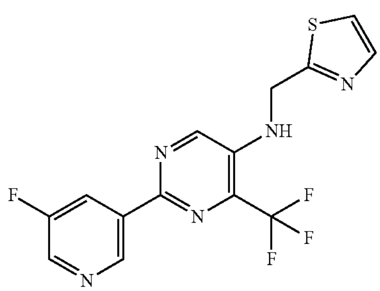 [SMILES: Fc1cncc(-c2ncc(NCc3nccs3)c(C(F)(F)F)n2)c1] | 9.35 (s, 1H), 8.57 (s, 1H), 8.50 (s, 1H), 8.30 (d, 1H), 7.81 (s, 1H), 7.38 (s, 1H), 5.60 (br s, 1H), 4.90 (d, 2H) |

Physical Characterisation

Compounds of the invention were characterised using one or more of the following methods.

NMR

NMR spectra contained herein were recorded on either a 400 MHz Bruker AVANCE III HD equipped with a Bruker SMART probe or a 500 MHz Bruker AVANCE III equipped with a Bruker Prodigy probe. Chemical shifts are expressed as ppm downfield from TMS, with an internal reference of either TMS or the residual solvent signals. The following multiplicities are used to describe the peaks: s=singlet, d=doublet, t=triplet, dd=double doublet, m=multiplet. Additionally br. is used to describe a broad signal and app. is used to describe and apparent multiplicity.

LCMS

LCMS data contained herein consists of the molecular ion [MH+] and the retention time (tr) of the peak recorded on the chromatogram. The following instruments, methods and conditions were used to obtain LCMS data:

Method A

Instrumentation: Waters Acquity UPLC-MS using a Sample Organizer with Sample Manager FTN, H-Class QSM, Column Manager, 2×Column Manager Aux, Photodiode Array (Wavelength range (nm): 210 to 400, ELSD and SQD 2 equipped with a Waters HSS T3 C18 column (column length 30 mm, internal diameter of column 2.1 mm, particle size 1.8 micron).

Ionisation method: Electrospray positive and negative: Capillary (kV) 3.00, Cone (V) 30.00, Source Temperature (° C.)

500, Cone Gas Flow (L/Hr.) 10, Desolvation Gas Flow (L/Hr.) 1000. Mass range (Da): positive 95 to 800, negative 115 to 800.

The analysis was conducted using a two minute run time, according to the following gradient table at 40° C.:

| Time (mins) | Solvent A (%) | Solvent B (%) | Flow (ml/mn) |
|---|---|---|---|
| 0.00 | 95.0 | 5.0 | 0.7 |
| 1.75 | 0.0 | 100 | 0.7 |
| 1.76 | 0.0 | 100 | 0.7 |
| 2.0 | 0.0 | 5.0 | 0.7 |
| 2.01 | 95.0 | 5.0 | 0.7 |
| 2.11 | 95.0 | 5.0 | 0.7 |

Solvent A: $H_2O$ with 0.05% TFA

Solvent B: $CH_3CN$ with 0.05% TFA

Method B (2 Min Method)

Instrumentation: Either (a) Waters Acquity UPLC system with Waters SQD2 single-quad MS detector, Photodiode Array Detector (Absorbance Wavelength: 254 nm, 10 pts/sec, Time Constant: 0.2000 sec), Charged Aerosol Detector (Corona) and Waters CTC 2770 auto-sampler unit (injection volume: 2 microliters, 1 min seal wash); or (b) Waters Acquity UPLC system with Waters QDa single-quad MS detector, Photodiode Array Detector (Absorbance Wavelength: 254 nm, 10 pts/sec, Time Constant: 0.2000 sec), Charged Aerosol Detector (Corona) and Waters CTC 2770 auto-sampler unit (injection volume: 2 microliters, 1 min seal wash).

LC-Method:

Phenomenex 'Kinetex C18 100A' column (50 mm×4.6 mm, particle size 2.6 micron),

Flow rate: 2 mL/min at 313K (40 Celsius),

Gradient (Solvent A: $H_2O$ with 0.1% Formic Acid; Solvent B: Acetonitrile with 0.1% Formic Acid):

The analysis was conducted using a two minute run time, according to the following gradient table at 40° C.

| Time (mins) | Solvent A (%) | Solvent B (%) | Flow (ml/mn) |
|---|---|---|---|
| Initial | 70.0 | 30.0 | 2.000 |
| 1.20 | 10.0 | 90.0 | 2.000 |
| 1.70 | 10.0 | 90.0 | 2.000 |
| 1.80 | 70.0 | 30.0 | 2.000 |
| 2.00 | 70.0 | 30.0 | 2.000 |
| 2.20 | 70.0 | 30.0 | 2.000 |

Method C (1 Min Method)

Instrumentation: Either (a) Waters Acquity UPLC system with Waters SQD2 single-quad MS detector, Photodiode Array Detector (Absorbance Wavelength: 254 nm, 10 pts/sec, Time Constant: 0.2000 sec), Charged Aerosol Detector (Corona) and Waters CTC 2770 auto-sampler unit (injection volume: 2 microliters, 1 min seal wash); or (b) Waters Acquity UPLC system with Waters QDa single-quad MS detector, Photodiode Array Detector (Absorbance Wavelength: 254 nm, 10 pts/sec, Time Constant: 0.2000 sec), Charged Aerosol Detector (Corona) and Waters CTC 2770 auto-sampler unit (injection volume: 2 microliters, 1 min seal wash).

LC-Method:

Phenomenex 'Kinetex C18 100A' column (50 mm×4.6 mm, particle size 2.6 micron), Flow rate: 2 mL/min at 313K (40 Celsius), Gradient (Solvent A: $H_2O$ with 0.1% Formic Acid; Solvent B: Acetonitrile with 0.1% Formic Acid):

The analysis was conducted using a one minute run time, according to the following gradient table at 40° C.

| Time (mins) | Solvent A (%) | Solvent B (%) | Flow (ml/mn) |
|---|---|---|---|
| Initial | 60.0 | 40.0 | 2.000 |
| 0.80 | 0.0 | 100.0 | 2.000 |
| 0.95 | 0.0 | 100.0 | 2.000 |
| 1.00 | 60.0 | 40.0 | 2.000 |
| 1.10 | 60.0 | 40.0 | 2.000 |
| 1.25 | 60.0 | 40.0 | 2.000 |

BIOLOGICIAL EXAMPLES

B1 Pre-Emergence Herbicidal Activity

Seeds of a variety of test species were sown in standard soil in pots: *Triticum aestivium* (TRZAW), *Avena fatua* (AVEFA), *Alopecurus myosuroides* (ALOMY), *Echinochloa crus-galli* (ECHCG), *Lolium perenne* (LOLPE), *Zea Mays* (ZEAMX), *Abutilon theophrasti* (ABUTH), *Amaranthus retroflexus* (AMARE) and *Setaria faberi* (SETFA). After cultivation for one day (pre-emergence) under controlled conditions in a glasshouse (at 24/16° C., day/night; 14 hours light; 65% humidity), the plants were sprayed with an aqueous spray solution derived from the formulation of the technical active ingredient in acetone/water (50:50) solution containing 0.5% Tween 20 (polyoxyethelyene sorbitan monolaurate, CAS RN 9005-64-5). The test plants were then grown in a glasshouse under controlled conditions (at 24/16° C., day/night; 14 hours light; 65% humidity) and watered twice daily. After 13 days, the test was evaluated (5=total damage to plant; 0=no damage to plant). Results are shown in Tables B1a and B1b.

Tables B1a and B1b Control of Weed Species by Compound of Formula (I) After Pre-Emergence Application TABLE B1a

| | | Test 1a | | | | | |
|---|---|---|---|---|---|---|---|
| Compound ID | Rate (g/ha) | AMARE | ABUTH | SETFA | LOLPE | ECHCG | ZEAMX |
| D1 | 1000 | 1 | 1 | 3 | 0 | 1 | 0 |
| D2 | 1000 | 1 | 1 | 2 | 0 | 1 | 0 |

TABLE B1b

| | | Test 1b | | | | | |
|---|---|---|---|---|---|---|---|
| Compound ID | Rate (g/ha) | ECHCG | LOLPE | SETFA | AVEFA | ALOMY | TRAZW |
| D3 | 1000 | 1 | 1 | 2 | 0 | 0 | 0 |
| D4 | 1000 | 0 | 1 | 2 | 0 | 0 | 0 |
| D5 | 1000 | 4 | 1 | 5 | 4 | 1 | 0 |

TABLE B1b-continued

Test 1b

| Compound ID | Rate (g/ha) | ECHCG | LOLPE | SETFA | AVEFA | ALOMY | TRAZW |
|---|---|---|---|---|---|---|---|
| D6 | 1000 | 4 | 1 | 4 | 1 | 0 | 0 |
| D7 | 1000 | 2 | 1 | 4 | 1 | 0 | 0 |
| D8 | 1000 | 2 | 1 | 4 | 1 | 0 | 0 |
| D9 | 1000 | 3 | 1 | 4 | 2 | 0 | 0 |
| D10 | 1000 | 0 | 0 | 3 | 0 | 0 | 0 |
| D11 | 1000 | 3 | 0 | 5 | 0 | 0 | 0 |
| D12 | 1000 | 1 | 0 | 5 | 0 | 0 | 0 |
| D13 | 1000 | 1 | 1 | 2 | 0 | 0 | 1 |
| D14 | 1000 | 2 | 1 | 2 | 0 | 1 | 1 |
| D15 | 1000 | 4 | 0 | 5 | 1 | 0 | 0 |

B2 Post-Emergence Herbicidal Activity

Seeds of a variety of test species were sown in standard soil in pots: *Triticum aestivium* (TRZAW), *Avena fatua* (AVEFA), *Alopecurus myosuroides* (ALOMY), *Echinochloa crus-galli* (ECHCG), *Lolium perenne* (LOLPE), *Zea Mays* (ZEAMX), *Abutilon theophrasti* (ABUTH), *Amaranthus retroflexus* (AMARE) and *Setaria faberi* (SETFA). After 8 days cultivation (post-emergence) under controlled conditions in a glasshouse (at 24/16° C., day/night; 14 hours light; 65% humidity), the plants were sprayed with an aqueous spray solution derived from the formulation of the technical active ingredient in acetone/water (50:50) solution containing 0.5% Tween 20 (polyoxyethelyene sorbitan monolaurate, CAS RN 9005-64-5). The test plants were then grown in a glasshouse under controlled conditions (at 24/16° C., day/night; 14 hours light; 65% humidity) and watered twice daily. After 13 days, the test was evaluated (5=total damage to plant; 0=no damage to plant). Results are shown in Tables B2a and B2b.

Tables B2a and B2b Control of Weed Species by Compound of Formula (I) After Post-Emergence Application

TABLE B2a

Test B2a

| Compound ID | Rate (g/ha) | AMARE | ABUTH | SETFA | LOLPE | ECHCG | ZEAMX |
|---|---|---|---|---|---|---|---|
| D1 | 1000 | 0 | 0 | 3 | 1 | 2 | 1 |
| D2 | 1000 | 1 | 1 | 3 | 1 | 2 | 1 |

TABLE B2b

Test B2b

| Compound ID | Rate (g/ha) | ECHCG | LOLPE | SETFA | AVEFA | ALOMY | TRAZW |
|---|---|---|---|---|---|---|---|
| D3 | 1000 | 2 | 1 | 3 | 1 | 1 | 0 |
| D4 | 1000 | 1 | 1 | 1 | 0 | 1 | 0 |
| D5 | 1000 | 4 | 3 | 5 | 4 | 1 | 1 |
| D6 | 1000 | 5 | 3 | 5 | 2 | 0 | 1 |
| D7 | 1000 | 2 | 0 | 4 | 1 | 0 | 1 |
| D8 | 1000 | 4 | 0 | 5 | 1 | 0 | 0 |
| D9 | 1000 | 3 | 2 | 5 | 3 | 0 | 0 |
| D10 | 1000 | 3 | 1 | 4 | 1 | 0 | 1 |
| D11 | 1000 | 5 | 1 | 5 | 2 | 1 | 1 |
| D12 | 1000 | 5 | 2 | 5 | 3 | 0 | 1 |
| D13 | 1000 | 4 | 1 | 4 | 3 | 0 | 0 |
| D14 | 1000 | 4 | 2 | 4 | 3 | 1 | 0 |
| D15 | 1000 | 5 | 2 | 5 | NT | 1 | 0 |

The invention claimed is:

1. A method of selectively controlling weed, comprising applying a weed controlling amount of a compound of formula (I)

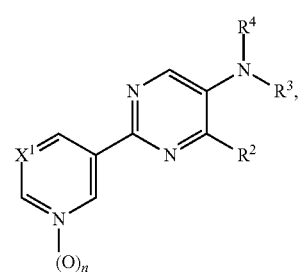

or a salt thereof, wherein:

$X^1$ is N or $CR^1$;

$R^1$ is selected from the group consisting of hydrogen, halogen, cyano, $C_1$-$C_6$alkyl, $C_3$-$C_6$cycloalkyl, $C_2$-$C_6$alkenyl, $C_2$-$C_6$alkynyl, $C_1$-$C_6$alkoxy, —C(O)OC$_1$-$C_6$alkyl, —S(O)$_p$C$_1$-$C_6$alkyl, $NR^6R^7$, $C_1$-$C_6$haloalkoxy and $C_1$-$C_6$haloalkyl;

$R^2$ is selected from the group consisting of halogen, cyano, nitro, $C_1$-$C_6$alkyl, $C_1$-$C_6$haloalkyl, $C_2$-$C_6$alkenyl, $C_2$-$C_6$alkynyl, $C_3$-$C_6$cycloalkyl, —C(O)OC$_1$-$C_6$alkyl, —S(O)$_p$(C$_1$-$C_6$alkyl), $C_1$-$C_6$alkoxy, $C_1$-$C_6$haloalkoxy and phenyl;

$R^3$ is selected from the group consisting of hydrogen, $C_1$-$C_6$alkyl, $C_2$-$C_6$alkenyl, $C_2$-$C_6$alkynyl, $C_2$-$C_6$haloalkenyl, $C_1$-$C_6$alkoxyC$_1$-$C_3$alkyl-, $C_1$-$C_6$haloalkyl- and —(CR$^a$R$^b$)$_q$R$^5$;

$R^a$ is hydrogen or $C_1$-$C_2$ alkyl;

$R^b$ is hydrogen or $C_1$-$C_2$ alkyl;

$R^4$ is hydrogen, $C_1$-$C_6$alkyl, $C_2$-$C_6$alkenyl, $C_2$-$C_6$alkynyl, $C_2$-$C_6$haloalkenyl, $C_1$-$C_6$alkoxyC$_1$-$C_3$alkyl-, $C_1$-$C_6$haloalkyl- and —(CR$^a$R$^b$)$_q$R$^5$;

$R^5$ is —C(O)OC$_1$-$C_6$alkyl, —C$_3$-$C_{10}$cycloalkyl, -aryl, or -heteroaryl wherein said aryl and heteroaryl are optionally substituted by 1 to 3 independent $R^8$;

or $R^3$ and $R^4$ together with the nitrogen to which they are attached, form a saturated or partially unsaturated 4-6 membered ring system optionally containing 1 or 2 further heteroatoms independently selected from S in the form S(O)$_p$, O and N, wherein said ring is optionally substituted by 1 to 3 $R^8$;

$R^6$ and $R^7$ are independently selected from the group consisting of hydrogen, $C_1$-$C_6$alkyl and —C(O)OC$_1$-$C_6$alkyl;

each $R^8$ is independently selected from the group consisting of halogen, $C_1$-$C_6$ alkyl and $C_1$-$C_6$alkoxy-, $C_1$-$C_6$ haloalkyl, $C_1$-$C_6$ haloalkoxy-, cyano and $S(O)_p(C_1$-$C_6$alkyl);

n is 0 or 1;

p is 0, 1, or 2; and q is 0, 1, or 2, and when q is 0, $R^5$ is not —C(O)O$C_1$-$C_6$alkyl, to a weed or a locus of the weed.

2. The method of claim 1, wherein the compound of Formula (I) is:

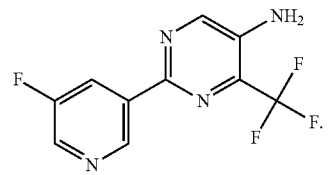 [SMILES: Nc1cnc(-c2cncc(F)c2)nc1C(F)(F)F]

3. The method of claim 1, wherein $R^3$ and $R^4$ are H.
4. The method of claim 1, wherein $R^2$ is $CF_3$.
5. The method of claim 3, wherein $R^2$ is $CF_3$.
6. The method of claim 1, wherein $X^1$ is N.
7. The method of claim 1, wherein the weed is a grassy weed.

* * * * *